(12) United States Patent
Kobiki et al.

(10) Patent No.: US 6,614,871 B1
(45) Date of Patent: Sep. 2, 2003

(54) MEDICAL X-RAY APPARATUS

(75) Inventors: Takaaki Kobiki, Noda (JP); Tsutomu Suzuki, Abiko (JP); Yutaka Takuma, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 0 days.

(21) Appl. No.: 09/937,319
(22) PCT Filed: Mar. 23, 2000
(86) PCT No.: PCT/JP00/01773
§ 371 (c)(1),
(2), (4) Date: Sep. 25, 2001
(87) PCT Pub. No.: WO00/57785
PCT Pub. Date: Oct. 5, 2000

(30) Foreign Application Priority Data

Mar. 26, 1999 (JP) ................................. 11/84869

(51) Int. Cl.[7] ................................. A61B 6/00
(52) U.S. Cl. ..................... 378/20; 378/4; 378/193; 378/195; 378/196; 378/197; 250/522.1
(58) Field of Search ................. 378/4, 20, 193, 378/197, 195, 196; 250/522.1

(56) References Cited

U.S. PATENT DOCUMENTS

| | | | | |
|---|---|---|---|---|
| 4,138,721 A | * | 2/1979 | Boyd | 378/14 |
| 4,628,523 A | * | 12/1986 | Heflin | 378/193 |

* cited by examiner

Primary Examiner—Drew A. Dunn
Assistant Examiner—Courtney Thomas
(74) Attorney, Agent, or Firm—Antonelli, Terry, Stout & Kraus, LLP

(57) ABSTRACT

To a supporting frame having an opening portion used to insert a table for mounting thereon an object under examination along a horizontal direction, a rotary member rotated around the opening portion is mounted; and a medical X-ray apparatus is provided with a first supporting member supported by the rotation member, for supporting an X-ray tube apparatus which irradiates an X-ray to an object under examination; a second supporting member for supporting a detection apparatus for detecting a transmission X-ray of the object under examination, the second supporting member being supported by the rotary member and being arranged opposite to the X-ray tube apparatus; a rotation control apparatus for controlling a rotation of the rotary member; a control apparatus for setting an irradiation angle of said X-ray with respect to a body axial direction of the object under examination to an arbitrary irradiation angle, and also for arranging the detection apparatus opposite to the X-ray tube apparatus in correspondence with the set arbitrary irradiation angle; and an image processing apparatus for processing an output signal from the detection apparatus so as to produce both a two-dimensional image and a three-dimensional image. While these control apparatus and rotation control apparatus are controlled, both the X-ray tube apparatus and the detection apparatus are rotated around the object under examination. Alternatively, X-ray fluoroscopic operation is carried out along an arbitrary irradiation angle. An output signal derived from the detection apparatus is processed by an image processing apparatus so as to produce a two-dimensional image and/or a three-dimensional image. Then, the produced images are displayed on a display apparatus.

35 Claims, 8 Drawing Sheets

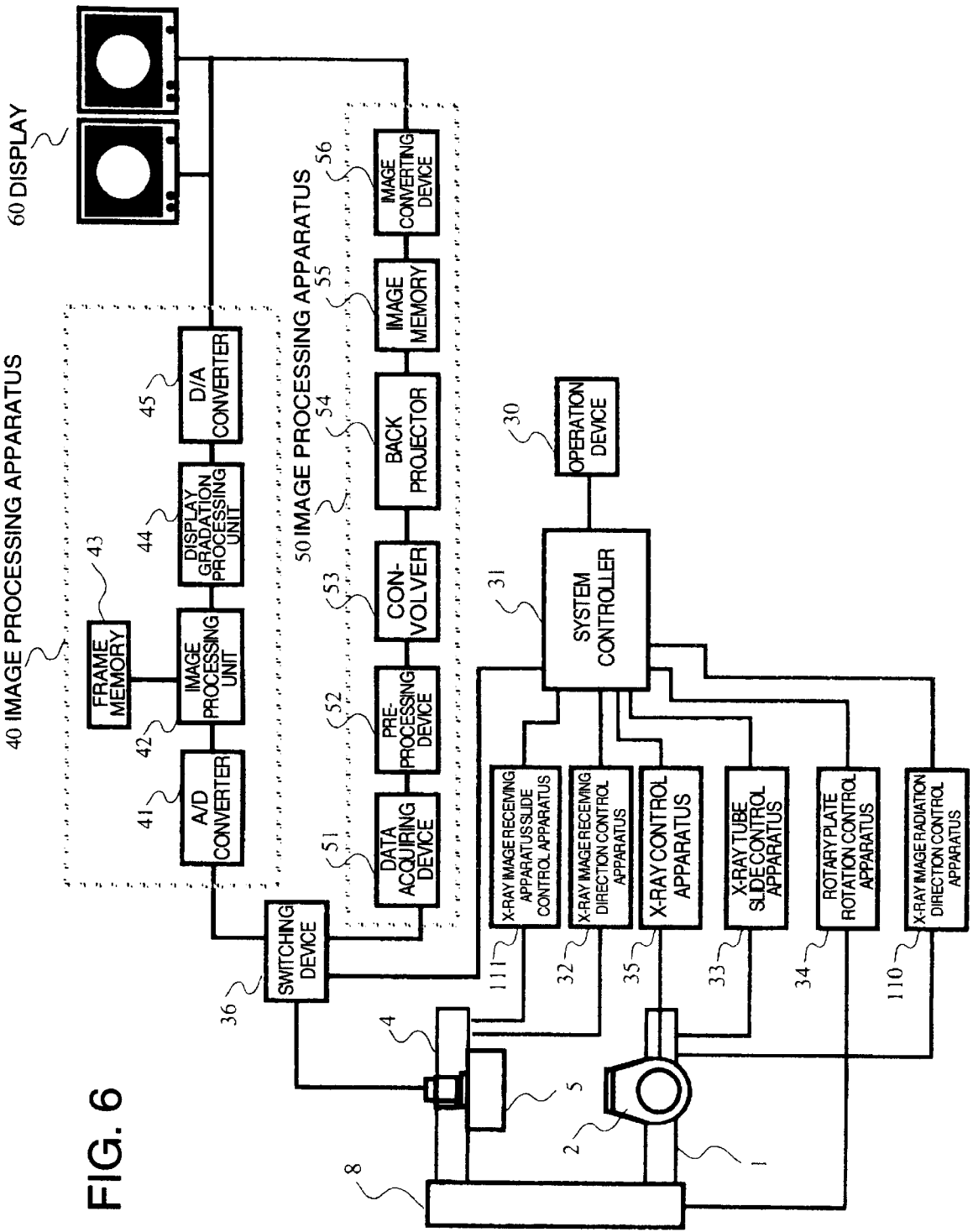

MEDICAL X-RAY APPARATUS

CROSS-REFERENCE TO RELATED APPLICATION

The present invention is related to a Patent Application entitled "RADIOGRAPHY APPARATUS", U.S. application Ser. No. 09/425,300, filed on Oct. 25, 1999, now U.S. Pat. No. 6,318,892 B1.

This U.S. patent application corresponds to Japanese Patent Application No. Hei-10-306238 filed on Oct. 28, 1998 in Japan. The disclosures of the above-described U.S. patent application are hereby incorporated into the present patent application by reference.

TECHNICAL FIELD

The present invention generally relates a medical X-ray apparatus. More specifically, the present invention is related to a medical X-ray apparatus having a function capable of acquiring both a two-dimensional image and a three-dimensional image by using one set of apparatus. This medical X-ray apparatus is suitable for a so-called "IVR (Interventional Radiology)" medical curing method with employment of an angiography and an X-ray diagnostic apparatus.

BACKGROUND ART

Medical X-ray fluoroscopic imaging apparatus such as X-ray fluoroscopic imaging tables and circulatory X-ray checking apparatus are necessarily required in diagnostic fields. Recently, these medical X-ray fluoroscopic imaging apparatus may be utilized not only in diagnostic purposes, but also in curing purposes. This curing operation may be carried out in such a manner that while observing X-ray fluoroscopic images, catheters equipped with various instruments at tip portions thereof are inserted into blood vessels and organs of objects under medical examination. This medical X-ray apparatus is capable of having such great merits of giving small pain to the objects under examination, as well as of executing low-cost curing operations with respect to such conventional curing operations in which celiotomy should be performed. As a consequence, very recently, this sort of medical X-ray apparatus are rapidly popularized. Such a curing method is referred to as an "IVR (Interventional Radiology)."

When this IVR method is carried, an operator confirms both a relative position of a portion to be cured and a shape thereof by using a three-dimensional X-ray image of this curing portion prior to an operation of this curing portion. Next, while the operator confirms a position of a curing instrument mounted on a tip portion of a catheter by way of a two-dimensional X-ray fluoroscopic image, the operator may perform this IVR method.

With respect to such an IVR method, conventionally, such an X-ray apparatus called as an X-ray rotation three-dimensional imaging apparatus is employed so as to execute this IVR method. For example, the X-ray rotation three-dimensional imaging apparatus is described in JP-A-6-327663, and is provided with the imaging system which is arranged by the X-ray source for irradiating the cone beam-shaped X-ray, the X-ray image intensifier (will be referred to as an "X-ray I.I." hereinafter), and the television camera.

In this X-ray rotation three-dimensional imaging apparatus, since the object under examination is required to be installed in the cavity portion provided in the gantry having the large volume, the accesses to the object under examination by the operator along the omnidirection are restricted. As a result, it is not possible to secure a sufficiently large work space where the operator may perform the curing operations in the smooth manner.

Also, although this X-ray rotation three-dimensional imaging apparatus can perform the two-dimensional X-ray fluoroscopic imaging operation, the fluoroscopic direction is limited only to the direction perpendicular to the body axis of the object under examination. However, this X-ray rotation three-dimensional imaging apparatus cannot perform the two-dimensional X-ray fluoroscopic imaging operation along such an omnidirection as a direction oblique to the body axis, which is required in the IVR method.

DISCLOSURE OF THE INVENTION

In an IVR method, while both a position of a curing portion and a shape thereof of an object under medical examination are grasped by way of a three-dimensional image, this grasped curing portion is cured by observing two-dimensional fluoroscopic images acquired along an omnidirection.

Therefore, an object of the present invention is to provide a medical X-ray apparatus capable of varying a fluoroscopic angle with respect to a body axial direction of an object under medical examination, and capable of acquiring both a three-dimensional image and a two-dimensional image by the same apparatus, and further suitable for an IVR method.

The above-described object may be achieved by providing: a supporting member having an opening portion used to insert a table for mounting an object under examination along a body axial direction of the object under examination; a rotation member supported by the supporting member and rotated around the opening portion; a rotation control apparatus for controlling a rotation of the rotary member; a first supporting member supported by the rotation member, for supporting an X-ray tube apparatus which irradiates an X-ray to an object under examination; a second supporting member for supporting a detection apparatus for detecting a transmission X-ray of the object under examination, the second supporting member being supported by the rotary member and being arranged opposite to the X-ray tube apparatus; an image processing apparatus for processing an output signal from the detection apparatus so as to produce both a two-dimensional image and a three-dimensional image; a display apparatus for displaying the image produced by the image processing apparatus; and a control apparatus for setting an irradiation angle of the X-ray with respect to a body axial direction of the object under examination to an arbitrary irradiation angle, and also for arranging the detection apparatus opposite to the X-ray tube apparatus in correspondence with the set arbitrary irradiation angle. The control apparatus is arranged by an X-ray tube apparatus control apparatus for transporting the X-ray tube apparatus to an arbitrary position on the first supporting member so as to arbitrarily set an irradiation angle of an X-ray with respect to the body axial direction of the object under examination; and a detection apparatus control apparatus for controlling that the angle of the detection apparatus is located opposite to the X-ray tube apparatus in response to the irradiation angle set by the X-ray tube control apparatus. The X-ray tube apparatus control apparatus is arranged by an X-ray tube apparatus transporting apparatus for transporting the X-ray tube apparatus to an arbitrary position on the first supporting member; and an irradiation angle control apparatus for arbitrarily setting the irradiation angle of the X-ray tube apparatus at the arbitrary transported position. The detection apparatus control apparatus is arranged by a detection apparatus transporting apparatus for transporting the detection apparatus to an arbitrary position on the second supporting member; and an opposite-arrangement control apparatus for arranging the detection apparatus opposite to the X-ray tube apparatus at this transported position at the irradiation angle.

Both the X-ray tube apparatus control apparatus and the detection apparatus control apparatus are arranged by, for example, the below-mentioned items (1) and (2):

(1) The shape of the first supporting member for supporting the X-ray tube and the shape of the second supporting member for the detection apparatus are formed in arc shapes in order that both the X-ray tube apparatus and the detection apparatus may maintain the opposite positional relationship at any positions on the first supporting member and the second supporting member. Furthermore, such an apparatus is provided by which both the X-ray tube apparatus and the detection apparatus can be transported to any arbitrary positions on the first supporting member and the second supporting member.

(2) Both the first supporting member and the second supporting member are formed in straight-line shapes. Furthermore, there are provided: an apparatus capable of transporting both the X-ray tube apparatus and the detection apparatus to arbitrary positions on the first supporting member and the second supporting member; and also another apparatus capable of changing both the X-ray irradiation direction from the X-ray tube apparatus and the detection direction of the detection apparatus opposite to this irradiation direction in order that the X-ray tube apparatus and the detection apparatus can establish the opposite positional relationship between them at the transported positions by the transporting apparatus.

With employment of such an arrangement, the irradiation angle of the X-ray with respect to the body axial direction of the object under examination can be arbitrarily set, and also, the X-ray image receiving apparatus is arranged opposite to this set irradiation angle. As a consequence, the X-ray fluoroscopic imaging operations can be carried out along the omnidirection with respect to the body axial direction of the object under examination. Also, the IVR method can be carried out based upon the above-described three-dimensional image with reference to the two-dimensional fluoroscopic images acquired along the omnidirection. As a result, the positional information and also the shape information as to the blood vessels mixed with each other in the complex manner and the organs can become rich, so that operabilities of the diagnostic operations and of the curing operations can be improved.

Also, the above-described object of the present invention may be achieved by comprising: a rotary member rotatably supported by a supporting frame; a rotation control apparatus for controlling a rotation of the rotary member; a first supporting member supported by the rotation member, for supporting an X-ray tube apparatus which irradiates an X-ray to an object under examination; a second supporting member for supporting a detection apparatus for detecting a transmission X-ray of the object under examination, the second supporting member being supported by the rotary member and being arranged opposite to the X-ray tube apparatus; a control apparatus for setting an irradiation angle of the X-ray with respect to a body axial direction of the object under examination to an arbitrary irradiation angle, and also for arranging the detection apparatus opposite to the X-ray tube apparatus in correspondence with the set arbitrary irradiation angle; an image processing apparatus for processing an output signal from the detection apparatus so as to produce both a two-dimensional image and a three-dimensional image; and a display apparatus for displaying the image produced by the image processing apparatus.

The control apparatus is arranged by an X-ray tube apparatus control apparatus for transporting the X-ray tube apparatus to an arbitrary position on the first supporting member so as to arbitrarily set an irradiation angle of an X-ray with respect to the body axial direction of the object under examination; and a detection apparatus control apparatus for controlling that the angle of the detection apparatus is located opposite to the X-ray tube apparatus in response to the irradiation angle set by the X-ray tube control apparatus. The X-ray tube apparatus control apparatus is arranged by an X-ray tube apparatus transporting apparatus for transporting the X-ray tube apparatus to an arbitrary position on the first supporting member; and an irradiation angle control apparatus for arbitrarily setting the irradiation angle of the X-ray tube apparatus at the arbitrary transported position. The detection apparatus control apparatus is arranged by a detection apparatus transporting apparatus for transporting the detection apparatus to an arbitrary position on the second supporting member; and an opposite-arrangement control apparatus for arranging the detection apparatus opposite to the X-ray tube apparatus at this transported position at the irradiation angle.

Both the X-ray tube apparatus control apparatus and the detection apparatus control apparatus are arranged by, for example, the below-mentioned items (3) and (4):

(3) The shape of the first supporting member and the shape of the second supporting member are formed in arc shapes in order that both the X-ray tube apparatus and the detection apparatus may maintain the opposite positional relationship at any positions on the first supporting member and the second supporting member. Furthermore, such an apparatus is provided by which both the X-ray tube apparatus and the detection apparatus can be transported to any arbitrary positions on the first supporting member and the second supporting member.

(4) Both the first supporting member and the second supporting member are formed in straight-line shapes. Furthermore, there are provided: an apparatus capable of transporting both the X-ray tube apparatus and the detection apparatus to arbitrary positions on the first supporting member and the second supporting member; and also another apparatus capable of changing both the X-ray irradiation direction from the X-ray tube apparatus and the detection direction of the detection apparatus opposite to this irradiation direction in order that the X-ray tube apparatus and the detection apparatus can establish the opposite positional relationship between them at the transported positions by the transporting apparatus.

When the medical X-ray apparatus is arranged by employing the above-explained arrangement, the lengths of the first and second supporting members are made longer than those of such a case that the opening portion is formed on the supporting frame and the rotary member. This opening portion is used to insert the object under examination. As a result, this medical X-ray apparatus can accept the entire portion of this object under examination without moving the object under examination.

With employment of the above-explained arrangement, the X-ray fluoroscopic angle with respect to the body axial direction of the object under examination can also be varied, so that both the two-dimensional image and the three-dimensional images can be acquired by using the same apparatus along the multiple directions involving this fluoroscopic direction.

As a consequence, these two-dimensional images and three-dimensional images are displayed on either the same display apparatus or the separate display apparatus at the same time. While the operator observes these images, the operator can effectively perform both the diagnostic operation and the curing operation.

As previously described, in accordance with the present invention, while both the three-dimensional image and the two-dimensional image are produced by the same apparatus, the fluoroscopic imaging operation is carried out at an arbitrary angle with respect to the body axial direction of the object under examination based upon the positional information and the shape information as to the diagnostic portion and the curing portion of the object under examination with respect to the body axial direction of the object under examination. While referring to the two-dimensional fluoroscopic images acquired along the omnidirection, the operator can carry out the IVR method. As a consequence, such a medical X-ray apparatus can be provided which can contribute the improvements in the diagnostic operations and also the curing operations, since the positional information and the shape information as to the blood vessels mixed with each other in the complex manner and the organs can become rich.

BRIEF DESCRIPTION OF THE DRAWINGS

FIG. 6 is a structural diagram of a control apparatus according to the embodiment mode 2 of the present invention.

BEST MODE FOR CARRYING OUT THE INVENTION

Figure 1:
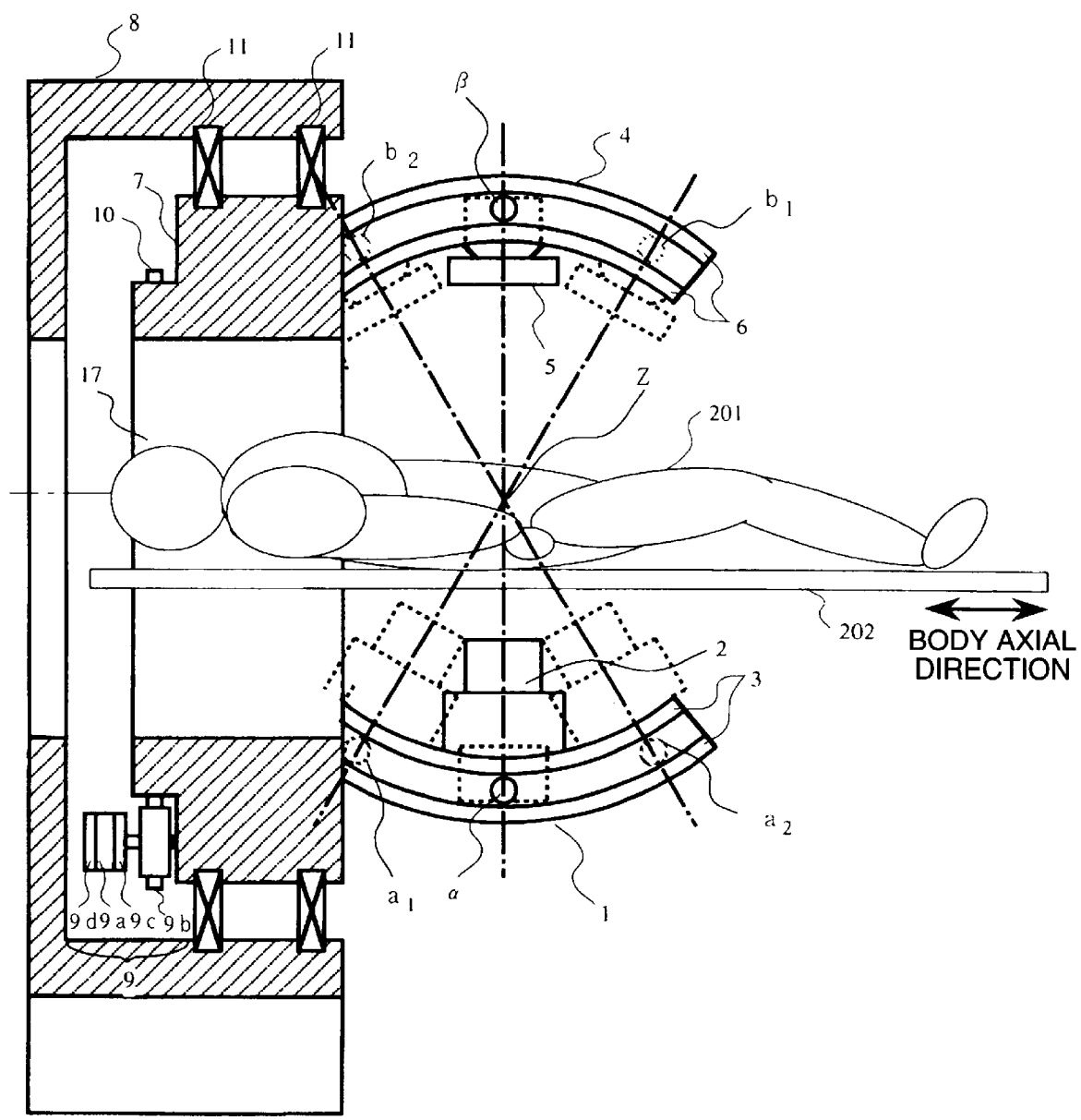
FIG. 1 is a schematic diagram for showing an arrangement of a medical X-ray apparatus according to an embodiment mode 1 of the present invention.

As a measure capable of solving the problem owned by the above-described X-ray rotary three-dimensional imaging apparatus, such an X-ray apparatus has been proposed in Japanese Patent Application No. Hei-10-306238 filed on Oct. 28, 1998. That is, while both a three-dimensional image of an object under medical examination and a two-dimensional image made by an X-ray fluoroscopy are produced by the same X-ray apparatus, this X-ray apparatus is capable of performing both an X-ray diagnosis and an X-ray curing method. This apparatus is provided with the apparatus capable of rotating the X-ray tube and the image receiving apparatus, while the X-ray tube corresponding to the X-ray source is mounted on one end of the supporting member, and the image receiving apparatus is mounted on the other end thereof. This X-ray apparatus forms a space at the rotation center portion, and is capable of acquiring the X-ray fluoroscopic data of the object under examination along the omnidirection. This X-ray apparatus is equipped with the X-ray image producing apparatus capable of producing not only the two-dimensional fluoroscopic image of the object under medical examination, but also the three-dimensional image thereof. This three-dimensional image corresponds to such a three-dimensional image of an arbitrary tomographic plane, and will be referred to as a "cone-beam CT image" hereinafter.

This X-ray apparatus forms the space in which the object under examination is relatively moved in the rotation center portion of the rotating apparatus for supporting the imaging system, and can transport the imaging area of the imaging system from the head portion up to the foot portion by merely horizontally transporting the object under examination in parallel to the rotation center axis of the above-explained rotating apparatus, or by merely transporting the rotating apparatus along the horizontal direction. As a result, this X-ray apparatus acquires the X-ray fluoroscopic data at an arbitrary position along the omnidirection, and then, enters this acquired X-ray fluoroscopic data into the X-ray image producing apparatus, so that the three-dimensional image of the imaging portion can be obtained by executing the well-known reconstruction calculation. Also, as to the two-dimensional image, when the fluoroscopic direction of the curing portion is determined based upon the above-explained three-dimensional image, the rotation position of the supporting member is fixed on the position of this fluoroscopic direction, and the X-ray fluoroscopic operation is carried out along the direction determined at this rotation position to acquire the two-dimensional image.

The position and the shape of the curing position of the object under examination is grasped based upon the three-dimensional image by way of such an X-ray apparatus. While the two-dimensional image is observed, the curing operation is carried out based upon this position and shape. This curing result is confirmed by producing the three-dimensional image by way of the above-explained method without moving the object under examination at this place.

However, the X-ray apparatus which has been proposed in Japanese Patent Application No. Hei-10-306238 can perform the X-ray fluoroscopic operation along an arbitrary angle direction (namely, direction perpendicular to body axis of object under examination) on the rotation center. However, the X-ray apparatus cannot be slide-transported along the direction (namely, body-axial direction of object) horizontally located with respect to the supporting member.

As a result, since the X-ray apparatus is inclined with respect to the body-axial direction of the object under examination and cannot perform the X-ray fluoroscopic operation along this inclined direction, this X-ray apparatus cannot observe the curing portion along these directions. There is such a problem that the curing range by way of the IVR is limited. In other words, since the X-ray apparatus does not own such a function that while both the X-ray source and the X-ray image receiving apparatus are inclined along the body-axial direction of the object under examination so as to position these X-ray source and X-ray image receiving apparatus in an opposite manner to each other, there are certain opportunities that the blood vessels and the like cannot be drawn along the above-explained fluoroscopic direction.

Therefore, while the present invention has been made to solve the above-described problem, the present invention is directed to provide such a medical X-ray apparatus suitable for the IVR, by which both a three-dimensional image and a two-dimensional image of an object under examination can be acquired by the same apparatus, while an X-ray fluoroscopic angle with respect to a body-axial direction of the object under examination is variable.

Referring now to drawings, a detailed description is made of the present invention in conjunction with embodiment modes (embodiments) of the present invention. It should be understood that in all of drawings used to explain the embodiment modes of the present invention, the same reference numerals will be employed as those for denoting the same functions, and therefore, descriptions thereof are omitted.

FIG. 1 is a structural diagram of a medical X-ray apparatus according to an embodiment mode 1 of the present invention.

First, a description is made of the construction of the medical X-ray apparatus according to the embodiment mode 1 of the present invention with reference to FIG. 1.

In FIG. 1, reference numeral 1 shows an arc-shaped arm. The arc-shaped arm 1 supports an X-ray tube 2 for irradiating an X-ray to an object 201 under medical examination present on a table 202, and is fixed on a rotary plate 7 having an opening portion 17 into which the object under examination may be inserted. The X-ray tube 2 is arranged in such a manner that this X-ray tube 2 may be transported by a curved-line guide unit 3 over the arm 1 within a curvature plane where an iso-center "Z" is located as a center thereof.

Reference numeral 4 shows an arc-shaped arm fixed on the rotary plate 7. The arc-shaped arm 4 supports an X-ray image receiving apparatus 5. The X-ray image receiving apparatus 5 is arranged at a position opposite to the X-ray tube 2 with sandwiching the object under examination, and detects an X-ray which is penetrated through the object under examination so as to convert the detected X-ray into an electric signal. The X-ray image receiving apparatus 5 is arranged in such a manner that this X-ray image receiving apparatus 5 may be transported by a curved-line guide unit 6 over the arm 4 within the curvature plane where the iso-center "Z" is located as the center thereof, while this X-ray image receiving apparatus 5 is located opposite to the X-ray tube 2.

The above-described X-ray apparatus 5 is constructed of both an image intensifier and a television camera, or both the image intensifier and a CCD (charge-coupled device) camera. Alternatively, a flat panel type two-dimensional sensor using a semiconductor detector may employed as the X-ray image receiving apparatus. Also, an opening portion 17 having the same dimension as that of the rotary plate 7 is formed in a supporting frame 8 for supporting the rotary plate 7. While the object under examination is transported in parallel to the rotation center axis of the rotary plate 7 by also involving the spaces of these opening portions, the entire portion of the object under examination defined from the head up to the foot can be examined by way of the X-ray fluoroscopic operation and the X-ray imaging operation.

The rotary plate 7 is ratably supported via at least one pair of bearings 11 with respect to the supporting frame 8 for supporting this rotary plate. Rotation drive force derived from a drive unit 9 is transferred via a belt 10 to the bearings 11 so as to rotate the rotary plate 7. The drive unit 9 is constituted by a motor 9a fixed on the supporting frame 8, a pulley 9b fixed on the motor shaft of this motor 9a, a brake 9c used to stop rotations of the motor 9a, and a detector 9d for detecting a rotation number of the motor 9a.

The detector 9d detects the actual rotation number of the motor 9a, and then, the detection value is employed so as to control the rotary plate 7 at a predetermined rotation number (control apparatus is omitted). Since the medical X-ray apparatus is arranged in the above-explained manner, both the arm 1 and the arm 4, which are fixed on the rotary plate 7 can be rotated around an axial line as a center. This axial line is located parallel to the body axial direction involving the iso-center "Z", and further, both the X-ray image receiving apparatus 5 and the X-ray tube 2 are rotatable, while the X-ray image receiving apparatus 5 is located opposite to the X-ray tube 2.

Figure 2A:
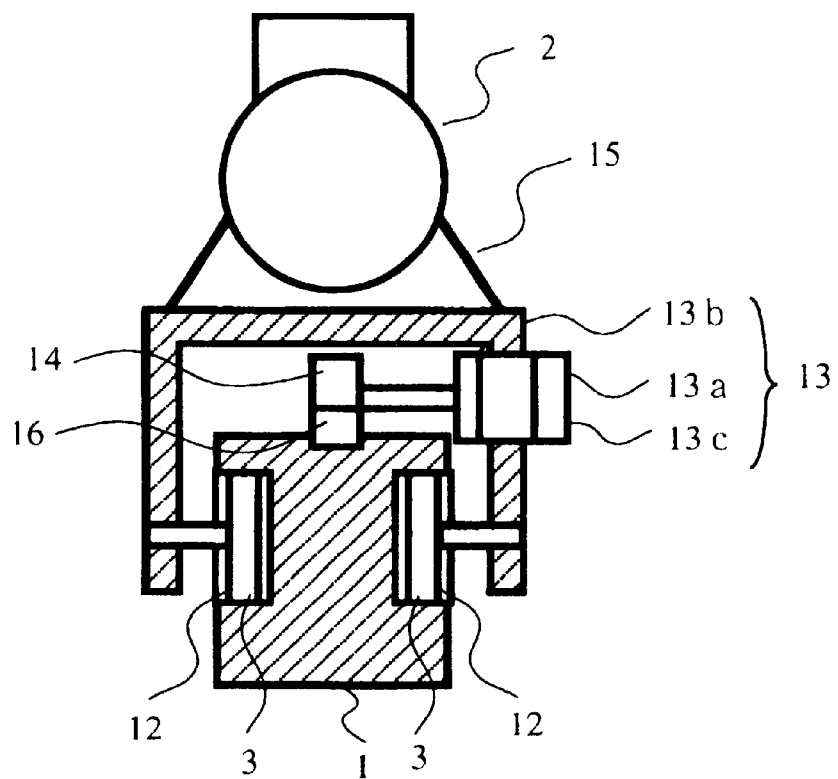
FIG. 2A and FIG. 2B are diagrams for representing a sliding transport mechanism for an X-ray tube and an X-ray image receiving apparatus according to the embodiment mode 1 of the present invention.
Figure 2B:
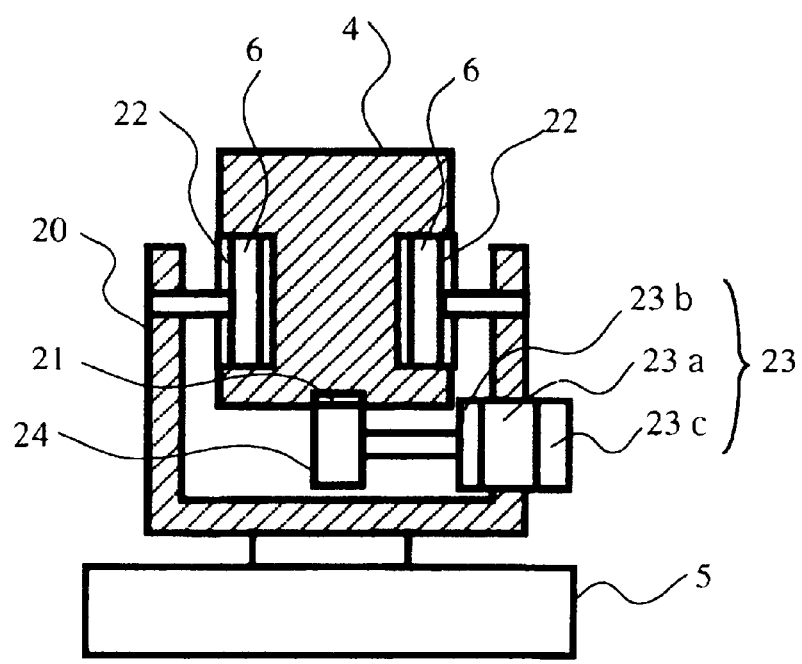
Figure 3:
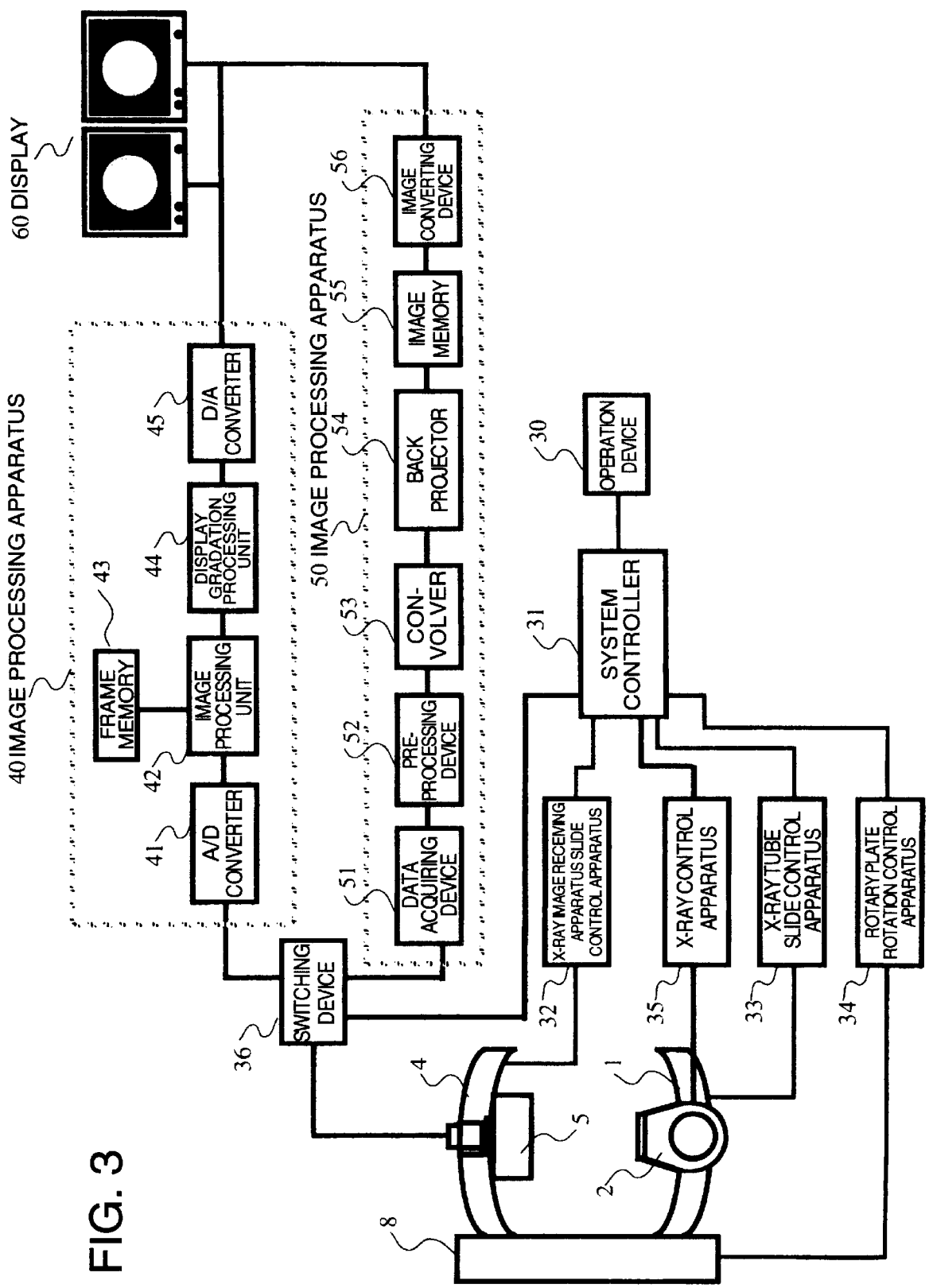
FIG. 3 is a structural diagram of a control apparatus according to the embodiment mode 1 of the present invention.

FIG. 2A and FIG. 2B show structural diagrams of a slide-transporting apparatus capable of slide-transporting the X-ray tube 2 and the X-ray image receiving apparatus 5, shown in FIG. 1, on the arc-shaped arms, respectively. That is, FIG. 2A is a structural diagram of a slide-transporting apparatus for the X-ray tube 2, and FIG. 2B is a structural diagram of a slide-transporting apparatus for the X-ray image receiving apparatus 5.

In FIG. 2A, the X-ray tube 2 is fixed on a frame 15, and the arm 1 is equipped with a curved-line guide unit 3 and an inner gear 16. At least one pair of rollers 12 are provided with the curved-line guide unit 3 of the arm 1. These rollers 12 can slide the curved-line guide unit 3 of the frame 15 with respect to this frame 15. This curved-line guide unit 3 is slid by receiving the drive force given from the drive unit 13.

The drive unit 13 is constituted by a motor 13a fixed on the frame 15, a brake 13b, a gear 14 which is fixed on a shaft end of the motor 13a and also a shaft end of the brake 13b, and a detector 13c for detecting the rotation number of the motor 13a. This drive unit 13 is arranged in such a manner that the drive force of the motor 13a is transferred to the curved-line guide unit 3 by the meshing the gear 14 fixed on the shaft end with the inner gear 16 provided in the arm 1.

On the other hand, in FIG. 2B, the X-ray image receiving apparatus 5 is fixed on a frame 20, and the arm 4 is equipped with a curved-line guide unit 6 and an inner gear 21. At least one pair of rollers 22 are provided with the curved-line guide unit 6 of the arm 4. These rollers 22 can slide the curved-line guide unit 6 of the frame 20 with respect to this frame 20. This curved-line guide unit 6 is slid by receiving the drive force given from the drive unit 23.

The drive unit 23 is constituted by a motor 23a fixed on the frame 20, a brake 23b, a gear 24 which is fixed on a shaft end of the motor 23a and also a shaft end of the brake 23b, and a detector 23c for detecting the rotation number of the motor 23a. This drive unit 23 is arranged in such a manner that the drive force of the motor 23a is transferred to the curved-line guide unit 6 by the meshing the gear 24 fixed on the shaft end with the inner gear 21 provided in the arm 4.

Next, operations of the embodiment mode 1 according to the present invention will now be described in detail with reference to FIG. 1, FIG. 2A, FIG. 2B, and FIG. 3 for representing an arrangement of a control apparatus of this medical X-ray apparatus.

An operator instructs an operation device 30 to select any one of an X-ray fluoroscopic image and a cone-beam CT image. In response to this instruction, when the operator selects the function of acquiring the fluoroscopic image, an output of the X-ray image receiving apparatus 5 is entered into an image processing apparatus 40 by operating a switching device 36. In response to this instruction, when the operator selects the function of acquiring the cone-beam CT image, an output of the X-ray image receiving apparatus 5 is entered to another image processing apparatus 50 by operating the switching device 36.

A: In the Case That the Function of Acquiring the X-ray Fluoroscopic Image is Selected In such a case that the operator selects the function of acquiring the fluoroscopic image, a system controller 31 supplies a command to the switching device 36 by which the output of the X-ray image receiving apparatus 5 is entered into the image processing apparatus 40 for processing the fluoroscopic image data, and also supplies a control command to an X-ray tube slide control apparatus 33, an X-ray image receiving apparatus slide-control apparatus 32, and a rotary plate control apparatus 34 to position the X-ray tube 2 and the X-ray image receiving apparatus 5 along a direction where the X-ray fluoroscopic operation is wanted to be carried out. The X-ray fluoroscopic operations according to the embodiment mode 1 of the present invention may be carried out by way of the below-mentioned methods along multiple directions in response to a diagnostic purpose and a curing purpose. Now, these operations will be explained as follows:

(A1) X-ray Fluoroscopic Operation Along Direction Perpendicular to Body Axis of Object Under Examination A slide position control command is sent from the operation device 30 via the system controller 31 to both the X-ray tube slide control apparatus 33 and the X-ray image receiving apparatus slide control apparatus 32. This slide position control command may slide-transport both the X-ray tube 2 and the X-ray image receiving apparatus 5 to such a position perpendicular to the body axis of the object under examination. Namely, this position corresponds to central positions (positions "α" and "β" of FIG. 1) of the arc-shaped arms 1 and 4 which supports the X-ray tube 2 and the X-ray image receiving apparatus 5.

In response to these slide position control commands, the motors (13a and 23a) of the drive units 13 and 23 for sliding the X-ray tube 2 and the X-ray image receiving apparatus 5 are rotated so as to rotate the gears (14 and 24) provided on the shaft ends of the motors. The frames 15 and 20 held under slidable condition are slid by the rollers (12 and 22) within the inner gears (16 and 21) which are meshed with these gears (14 and 24), so that both the X-ray tube 2 and the X-ray image receiving apparatus 5, which are supported by these frames (15 and 20) are arranged opposite to each other at such a position perpendicular to the body axis of the object under examination. In such a case that the X-ray tube 2 and the X-ray image receiving apparatus 5 are positioned to arbitrary rotation positions in order that the object under examination is treated by the X-ray fluoroscopic operation under this condition, or a traveling direction of a blood vessel is confirmed from another direction, an instruction is sent from the system controller 31 to the rotary plate rotation control apparatus 34 for controlling the rotation of the rotary plate 7 in response to an instruction of the operation device 30 operated by the operator in a manner similar to the above-described case. Based upon this instruction, the motor 9a of the drive unit 9 is rotated so as to rotate the pulley 9b coupled to this motor shaft. Then, the rotary plate 7 is rotated via the belt 10 which couples this pulley 9b to the rotary plate 7, and also via the bearing 11 for rotatably supporting the supporting frame 8. When the rotary plate 7 is reached to a target rotation angle position, the brake 9c is actuated so as to stop this rotary plate 7 at a desirable angle, so that both the X-ray tube 2 and the X-ray image receiving apparatus 5 are held under the stop condition. Then, the X-ray fluoroscopic operation is carried out with respect to the object under examination at this holding angle.

Then, both at the rotation angle position of the rotation plate 7 and in the slide positions of the X-ray tube 2 and the X-ray image receiving apparatus 5, the X-ray control apparatus 35 produces such an X-ray control amount used to generate X-rays corresponding to an X-ray condition supplied from the system controller 31 in response to an instruction issued from the operator by operating the operation device 30. The X-rays are generated by the X-ray tube 2 based upon the above-described control amount, and then, are irradiated to the object under examination. The X-rays which pass through this object under examination is entered into the X-ray image receiving apparatus 5 so as to be converted into an electric signal in an analog signal form. This analog signal is inputted to an A/D converter 41 of the image processing apparatus 40.

This analog signal is converted into a digital signal by the A/D converter 41, and then, this digital signal is supplied to the image processing unit 42 and also is stored into a frame memory 43. The image processing unit 42 executes such an image processing operation as a contract conversion and a gamma-characteristic conversion with respect to the digital image signal sent from the image processing unit 42, and then, supplies the image-processed digital image signal to a display gradation processing unit 44 for performing a gradation process operation. The digital image signal which has been gradation-processed by the display gradation processing unit 44 is converted into an analog image signal by a D/A converter 45, so that an X-ray fluoroscopic image may be represented on a display 60.

(A2) X-ray Fluoroscopic Operation from Direction Inclined with Respect to Body Axis of Object under Examination A slide position control command is sent from the operation device 30 via the system controller 31 to both the X-ray tube slide control apparatus 33 and the X-ray image receiving apparatus slide control apparatus 32. This slide position control command may slide-transport both the X-ray tube 2 and the X-ray image receiving apparatus 5 to positions other than positions inclined to the body axis of the object under examination which correspond to central positions (positions "α" and "β" of FIG. 1) of the arc-shaped arms 1 and 4 which support the X-ray tube 2 and the X-ray image receiving apparatus 5, respectively.

In response to these slide position control commands, the motors (13a and 23a) of the drive units 13 and 23 for sliding the X-ray tube 2 and the X-ray image receiving apparatus 5 are rotated so as to rotate the gears (14 and 24) provided on the shaft ends of the motors. The frames 15 and 20 held under slidable condition are slid by the rollers (12 and 22) within the inner gears (16 and 21) which are meshed with these gears (14 and 24), so that both the X-ray tube 2 and the X-ray image receiving apparatus 5, which are supported by these frames (15 and 20) are arranged opposite to each other at such a position inclined to the body axis of the object under examination. In such a case that the X-ray tube 2 and the X-ray image receiving apparatus 5 are positioned to arbitrary rotation positions in order that the object under examination is treated by the X-ray fluoroscopic operation under this condition, or a traveling direction of a blood vessel is confirmed from another direction, a similar operation to that of the above-described case (A1) is carried out.

Similar to the explanation of the above-described case (A1), an X-ray fluoroscopic image acquired from the direction inclined to the body axis of the object under examination is obtained by such that the X-ray fluoroscopic image data derived from the X-ray image receiving apparatus 5 is image-processed by the image processing apparatus 40, and thus, a desirable image is indicated on the display 60.

B: In the Case that the Function of Acquiring the Cone-beam X-ray Image is Selected In such a case that the operator selects the function of acquiring the cone beam CT image, the system controller 31 supplies a command to the switching device 36 by which the output of the X-ray image receiving apparatus 5 is entered into the image processing apparatus 50 for processing the cone-beam CT image data, and also supplies a control command to the X-ray tube slide control apparatus 33, and the X-ray image receiving apparatus slide-control apparatus 32 to position the X-ray tube 2 and the X-ray image receiving apparatus 5 in an opposite manner to each other. Also, the system controller 31 sends a rotary plate rotation control command to the rotary plate rotation control apparatus 34 to control the rotation of the rotary plate 7. A cone-beam CT image is photographed in response to these control commands. The cone-beam CT imaging method according to the embodiment mode 1 of the present invention is carried out by the following methods. Subsequently, operations of these cone-beam CT imaging methods will now be explained.

(B1). In Such a Case that Cone-beam CT Imaging Operation is Carried Out, While X-ray Tube 2 is Positioned Opposite to X-ray Image Receiving Apparatus 5 Perpendicular to Body Axis of Object Under Examination (on Vertical Line Involving Iso-center "Z"

A slide position control command is sent from the operation device 30 via the system controller 31 to both the X-ray tube slide control apparatus 33 and the X-ray image receiving apparatus slide control apparatus 32. This slide position control command may slide-transport both the X-ray tube 2 and the X-ray image receiving apparatus 5 to such positions perpendicular to the body axis of the object under examination. Namely, the positions correspond to central positions (positions "α" and "β" of FIG. 1) of the arc-shaped arms 1 and 4 which support the X-ray tube 2 and the X-ray image receiving apparatus 5, respectively.

In response to these slide position control commands, the motors (13a and 23a) of the drive units 13 and 23 for sliding the X-ray tube 2 and the X-ray image receiving apparatus 5 are rotated so as to rotate the gears (14 and 24) provided on the shaft ends of the motors. The frames 15 and 20 held under slidable condition are slid by the rollers (12 and 22) within the inner gears (16 and 21) which are meshed with these gears (14 and 24), so that the X-ray tube 2 which is supported by these frames (15 and 20) is at such a position of "α" on the arm 1 shown in FIG. 4 to be held, and also, the X-ray image receiving apparatus 5 is stopped at a position of "β" on the arm 4 shown in FIG. 1 to be held.

At a stage where a preparation for positioning of the object under examination is completed, the operator manipulates the operation device 30 so as to supply a rotation control command to the rotary plate rotation control apparatus 34 by the system controller 31 in order that the cone-beam CT image is photographed. In response to this rotation control command, the motor 9a of the drive unit 9 is rotated to rotate the rotary plate 7.

At such a time instant when the rotation speed of the rotary plate 7 is reached to a constant rotation speed, the system controller 31 controls the X-ray tube 2 via the X-ray control apparatus 35 to radiate X-rays. Then, the X-ray image receiving apparatus 5 detects X-rays which have passed through the object under examination while the rotary plate 7 is rotated by 1 turn, and then converts these detected X-rays into an electric signal.

The signal detected by the X-ray image receiving apparatus 5 is converted into a digital signal by the A/D converter, and also is stored into a data acquiring device 51. With respect to the X-ray image data derived from this data acquiring device 51, a pre-processing device 52 executes such a pre-processing operation as a logarithm conversion, a gain correction, and an offset correction. Then, the image data derived from this pre-processing device 52 is processed by a convolver 53 so as to calculate sum of products of X-ray absorption data along the forward projection direction.

Such a tomographic image is reconstructed by a back-projector 54, which is obtained by that data after the calculation of sum of products in the convolver 53 is back-projected with respect to an image memory 55 (will be discussed later) to be superimposed with each other. This reconstructed tomographic image is stored into the image memory 55. Then, such a three-dimensional image is indicated on the display 60. This three-dimensional image is produced by way of an image converter 56 which sets a CT value in a desirable range as to the data related to the tomographic image reconstructed on this image memory 55.

In accordance with this method, a three-dimensional image may be acquired. That is, this three-dimensional image owns a certain width of a sectional plane perpendicular to the body axis of the object under examination.

(B2). In Such a Case that Cone-beam X-ray CT Image is Acquired While Both X-ray Tube 2 and X-ray Image Receiving Apparatus 5 are Inclined with Respect to Body Axis of Object Under Examination While the X-ray image receiving apparatus 5 and the X-ray tube 2 are operated under control of the X-ray tube slide control apparatus 33 and the X-ray image receiving apparatus slide control apparatus 32, the rotary plate 7 is rotation-controlled by the rotary plate rotation control apparatus 34 to photograph a cone-beam X-ray CT image under such a condition that the X-ray tube 2 is located opposite to the X-ray image receiving apparatus 5 on a straight line having an arbitrary angle with respect to a vertical axial line involving an iso-center "Z" with respect to the iso-center "Z" as a center. This condition implies such positions (namely, positions other than "α" and "β" of FIG. 1) other than center positions of the arc-shaped arms 1 and 4 which support the X-ray tube 2 and the X-ray image receiving apparatus 5, respectively.

Similar to the above-described item (B1), as to a cone-beam CT image acquired along this direction, the image data derived from the X-ray image receiving apparatus 5 is processed by the image processing apparatus 50, and then, the processed image data is indicated on the display unit 60 as a three-dimensional image acquired from a direction inclined to the body axis of the object under examination.

(B3). In Such a Case that While X-ray Tube 2 and X-ray Image Receiving Apparatus 5 are Slid Along Opposite Directions Under Condition that Both X-ray Tube 2 and X-ray Image Receiving Apparatus 5 Maintain Opposite Positional Relationship, Rotary Plate 7 is Rotated to Photograph Cone-beam X-ray CT Image While the X-ray image receiving apparatus 5 and the X-ray tube 2 are operated under control of the X-ray tube slide control apparatus 33 and the X-ray image receiving apparatus slide control apparatus 32, the rotary plate 7 is rotated so as to acquire a cone-beam X-ray CT image under such a condition that the opposite positional relationship between the X-ray tube 2 and the X-ray image receiving apparatus 5 is maintained, and also this X-ray tube 2 and the X-ray image receiving apparatus 5 are slid along the opposite directions. For instance, while the X-ray tube 2 is arranged at a position "a1" of the right end of FIG. 1 and also the X-ray image receiving apparatus 5 is arranged at another position "b1" of the left end of FIG. 1, both the X-ray tube 2 and the X-ray image receiving apparatus 5 are mutually transported along the opposite directions by rotating the rotary plate 7 under such a condition that the opposite positional relationship between the X-ray tube 2 and the X-ray image receiving apparatus 5 is maintained in such a manner that the X-ray tube 2 is moved from the above position "a1" up to another position "a2", and the X-ray image receiving apparatus 5 is moved from the above position "b1" up to another position "b2."

In accordance with this method, since the image data can be acquired along the omnidirection by projecting the X-rays only one time, such a three-dimensional image corresponding to the multiple directions can be produced within one time by processing the acquired image data by the image processing unit 50. Then, this three-dimensional image can be indicated on the display unit.

(B4). In such a Case that Rotation Plate 7 is Rotated Under Such a Condition that X-ray Tube 2 and X-ray Image Receiving Apparatus 5 are Arranged at Arbitrary Positions and this Opposite Positional Relationship Between them is Maintained, Cone-beam X-ray CT Image is Acquired While Table 202 for Mounting Object Under Examination is Transported Along Body Axial Direction The rotation plate 7 is rotated under such a condition that the X-ray tube 2 and the X-ray image receiving apparatus 5 are arranged at arbitrary positions and further this opposite positional relationship between them is maintained, a cone-beam X-ray CT image may be acquired while the table 202 for mounting the object under examination is transported. According to this imaging method, since such a three-dimensional image of the object under examination over a wide range can be acquired within one time, the positional relationship between the curing portion of the object under examination and the portion adjacent to this curing portion can be made clear, so that the entire portion of the object under examination can be effectively grasped.

As a use example of the embodiment mode 1 of the present invention, a description will now be made of such a case that the medical X-ray apparatus of the embodiment mode 1 is employed in a blood vessel curing operation by using a catheter under X-ray fluoroscope corresponding to a typical example of the above-explained IVR. For example, in the case that infarction contained in a coronary artery, a catheter is inserted from a femoral vein, and this catheter is advanced to a blood vessel of interest under X-ray fluoroscope. Than, at the target portion, a constriction portion is dilated by using a balloon catheter, or an Atherectomy catheter.

First, in order to three-dimensionally grasp a position of a target portion and a shape of this target portion prior to the curing operation, the cone-beam CT function is selected to produce a three-dimensional image of this target portion, and this three-dimensional image is displayed on the display unit.

In this case, while three-dimensional images are produced from the omnidirection by executing the methods as explained in the above-explained (B1) to (B4), and then, these three-dimensional images are displayed on the display unit in the following manners. Referring to this displayed image, the position and the shape of the target portion can be correctly grasped.

(a). The three-dimensional images produced by the methods explained in the above-described items (B1) to (B4) are separately displayed.

(b). At least two sets of the three-dimensional images produced by the methods explained in the above-explained items (B1) to (B4) are displayed at the same time. For example, both the image photographed by that the X-ray tube 2 and the X-ray image receiving apparatus 5 are arranged opposite to each other perpendicular to the body axis of the object under examination (see item B1), and the image photographed by that the X-ray tube 2 and the X-ray image receiving apparatus 5 are inclined with respect to the body axis of the object under examination (see item B2) are displayed at the same time. Alternatively, either the image explained in the item (B1) or the image explained in the item (B2), and another image explained in the item (B3) are displayed at the same time. That is, as to the image of the item (B3), under such a condition that the opposite positional relationship between the X-ray tube 2 and the X-ray image receiving apparatus 5 is maintained, the rotary plate 7 is rotated to acquire the image (B3), while the X-ray tube 2 and the X-ray image receiving apparatus 5 are slid along the opposite directions.

Furthermore, many other images may be combined with each other for representation purposes.

These images may be displayed on the same display unit, or on different display units. Also, this simultaneous image display is not limited to two sorts of images, but more than two sorts of images may be displayed.

The traveling conditions of the blood vessels mixed with each other in complex manners are three-dimensionally observed based upon the images which are produced and displayed in this manner. Based upon this result, the catheter is manipulated to perform the dilating operation of the blood vessel under condition of infarction, while observing the fluoroscopic images acquired by the methods of the above-explained items (A1) and (A2). While this curing operation is carried out, the fluoroscopic images produced by the methods explained in the items (A1) and (A2) are solely displayed. In addition, both the fluoroscopic image acquired from the direction perpendicular to the body axis of the object under examination, and the fluoroscopic image acquired from the direction inclined to the body axis of the object under examination are displayed on either the same monitor, or the separate monitors. While referring to both the images displaying an arbitrary three-dimensional image selected from the above-explained cone-beam CT images and also the above-described fluoroscopic images are displayed on either the same display unit, or the separate display units, the operator can advance the curing operation by using these images as the guide purpose. Thereafter, after the curing operation is accomplished, the operator selects the cone-beam CT image so as to acquire a three-dimensional image, and then, can confirm the curing effects based upon this acquired three-dimensional image.

As previously described, in accordance with the embodiment mode 1 of FIG. 1, while the position and the shape of the target portion can be grasped by observing the three-dimensional image, the fluoroscopic angles along the multiple directions, especially, the fluoroscopic angle along the body axial direction can be arbitrarily set based upon these grasped results. As a result, the diagnostic information as to the blood vessels mixed with each other in the complex manner and the organs can become rich, by which the diagnosis and the curing operation can be improved.

Also, since the opening portion through which the object under examination is inserted is provided in the rotary plate, both the arc-shaped arms 1 and 4 can be made short as being permitted as possible, so that the medical X-ray apparatus can be made compact.

Figure 4:
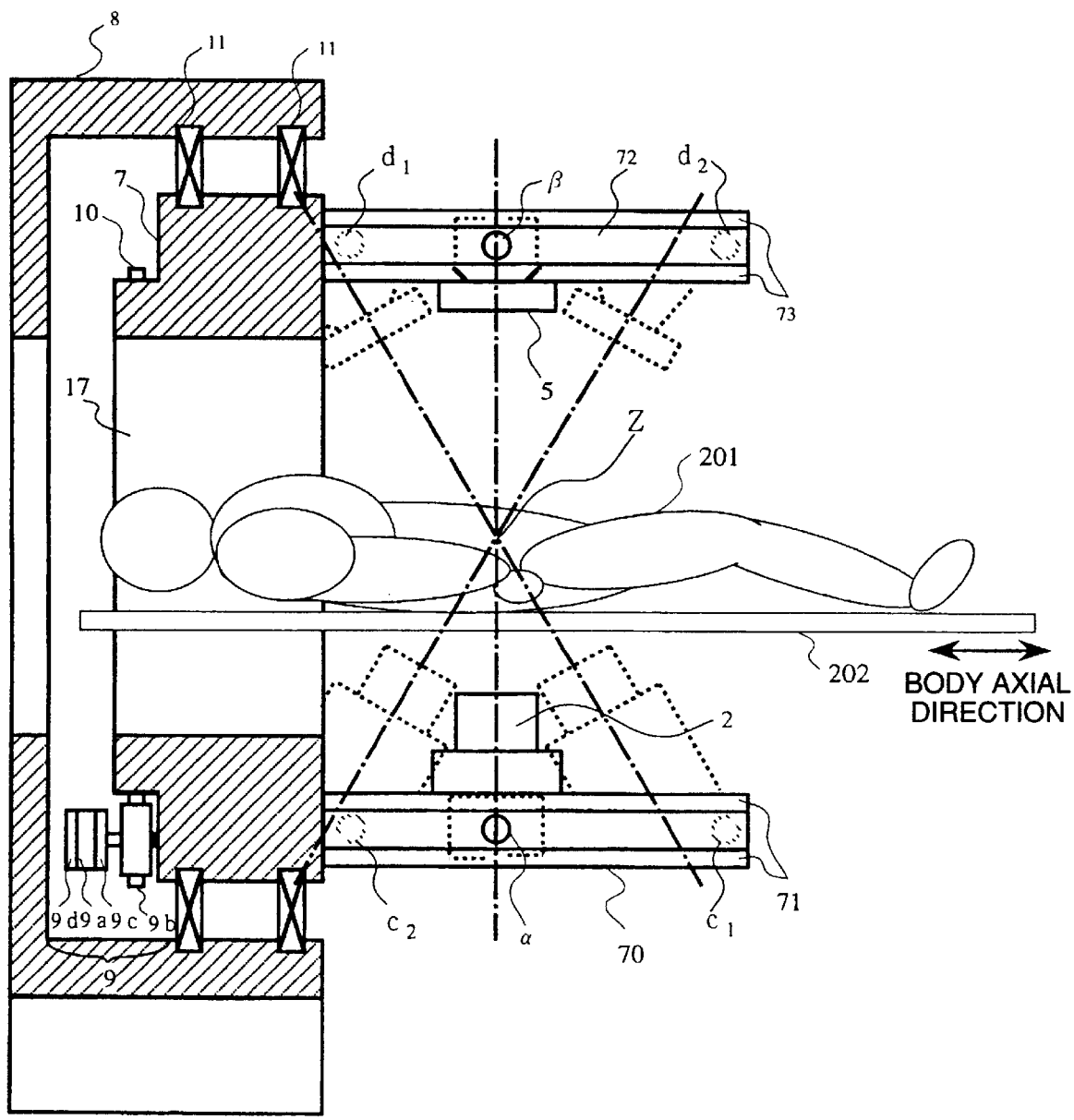
FIG. 4 is a schematic diagram for showing an arrangement of a medical X-ray apparatus according to an embodiment mode 2 of the present invention.

FIG. 4 is a structural diagram of a medical X-ray apparatus according to an embodiment mode 2 of the present invention.

This medical X-ray apparatus of the embodiment mode 2 shown in FIG. 4 is such an example that both an arm 70 and another arm 72 are made in straight-line shapes, which may slide/hold the X-ray tube 2 and the X-ray image receiving apparatus 5 at arbitrary positions. When the arm 70 and the arm 72 are made of the straight-line shapes, such an apparatus is required. This apparatus variably changes rotation angles of the X-ray tube 2 and the X-ray image receiving apparatus 5 in order to fluoroscopic-image an object under examination along a direction inclined to a body axis of the object under examination. FIG. 5 shows a structural construction having contrary both this rotation angle changing apparatus and also in means for slide-transporting the X-ray tube 2 and the X-ray image receiving apparatus 5. In FIG. 4, reference numeral 70 indicates a straight-line shaped arm which is fixed on the rotary plate 7 and supports the X-ray tube 2 for irradiating X-rays to an object 201 under examination. It is so constructed that the X-ray tube 2 is slidable on the arm 70 in a straight line manner by a straight-line guide unit 71.

Reference numeral 72 indicates another straight-line shape arm for supporting the X-ray image receiving apparatus 5, which is fixed on the rotary plate 7. The X-ray image receiving apparatus 5 is arranged at the position opposite to the X-ray tube 2, while sandwiching the object under examination, and detects an X-ray which has passed through the object under examination, and then, converts this detection signal into an electric signal. The X-ray image receiving apparatus 5 is arranged in such a manner that this X-ray image receiving apparatus 5 is slidable over the arm 72 in a linear fashion by way of a straight-line guide unit 73, while being located opposite to the X-ray tube 2.

The rotary plate 7 is rotatably supported via at least one pair of bearings 11 with respect to the supporting frame 8 for supporting this rotary plate 7. Rotation drive force derived from the drive unit 9 is transferred via a belt 10 to the bearing 11 so as to rotate the rotary plate 7. Similar to the above-described embodiment mode 1, an opening portion 17 into which the object under examination may be inserted is provided to the rotary plate 7 and the supporting frame 8.

The construction of the drive unit 9 is similar to that of FIG. 1. Since such a construction is employed, both the arm 70 and the arm 72, which are fixed on the rotary plate 7, may be rotated around a horizontal axial line involving the iso-center "Z" as a center, so that both the X-ray image receiving apparatus 5 and the X-ray tube 2 can be rotated, while the X-ray tube 2 is located opposite to the X-ray image receiving apparatus 5.

Figure 5A:
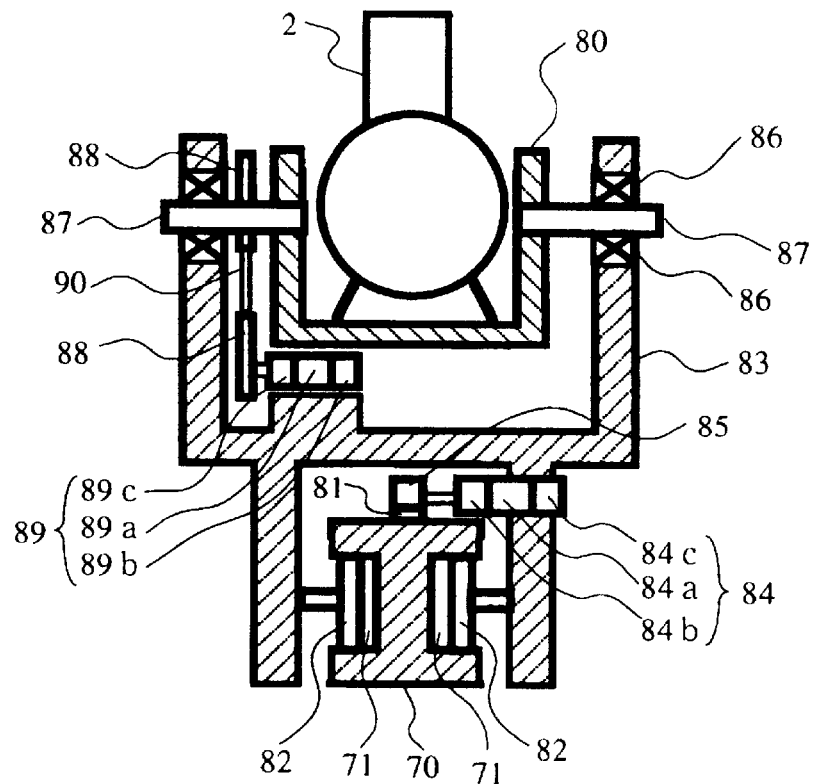
FIG. 5A and FIG. 5B are diagrams for representing a sliding transport mechanism for an X-ray tube and an X-ray image receiving apparatus according to the embodiment mode 2 of the present invention.
Figure 5B:
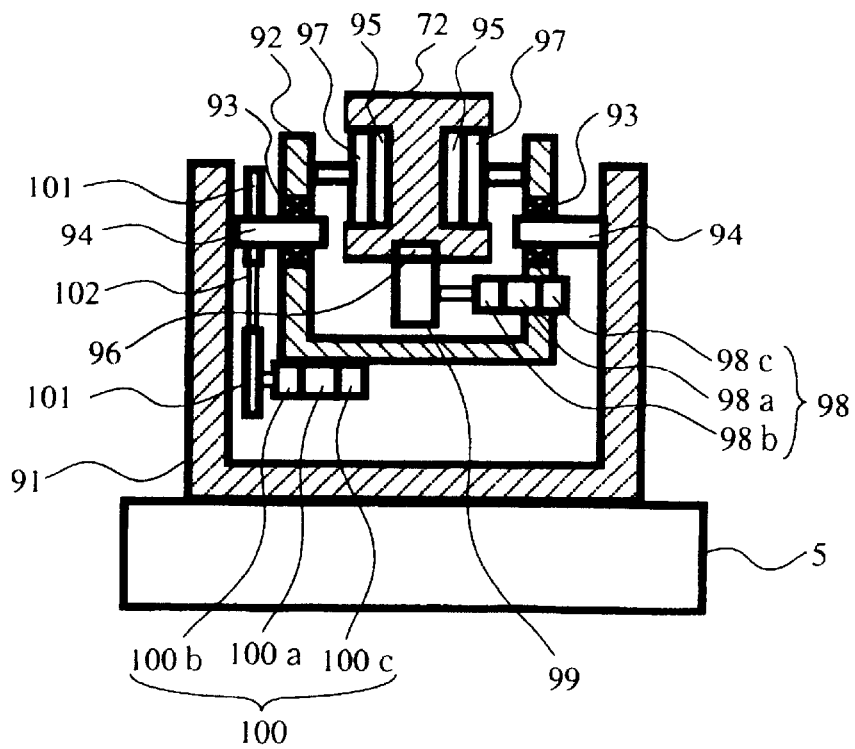

FIG. 5A and FIG. 5B are diagrams for representing a construction of a drive apparatus (sliding and rotating operations) of the X-ray tube 2 shown in FIG. 4, and also a construction of a drive apparatus (sliding and rotating operations) of the X-ray image receiving apparatus 5. That is, FIG. 5A is a structural diagram of the drive apparatus for driving the X-ray tube 2, and FIG. 5B is a structural diagram of the drive apparatus for driving the X-ray image receiving apparatus 5. First, a description is made of the drive apparatus for the X-ray tube 2. In FIG. 5A, the X-ray tube 2 is fixed on a rotary frame 80, and this rotary frame 80 is fitted to a slide frame 83 by way of a bearing 86 and a shaft 87. This slide frame 83 slides the X-ray tube 2 on a straight line of the arm 70.

The arm 70 owns both a straight line guide unit 71 and an inner gear 81, at least one pair of rollers 82 are provided in the straight line guide unit 81 of the arm 70, and this roller 82 can slide the straight-line guide unit 71 of the arm 70 with respect to the slide frame 83.

A slide drive unit 84 of the above-described slide apparatus is arranged by a motor 84a fixed on the slide frame 83, a brake 84b, a gear 85 fixed on a shaft end of this motor 84a, and also a detector 84c for detecting a rotation number of the motor 84a. The X-ray tube 2 is slid/transported by meshing the gear 85 fixed on the shaft end with the inner gear 81 provided on the arm 70.

The irradiation direction of the X-ray irradiated from the X-ray tube 2 in order to change the fluoroscopic direction is variable by rotating the rotary frame 80 by employing the below-mentioned mechanism. In other words, the rotary frame 80 is fixed on one end of a shaft 87 having an outer diameter which is made substantially coincident with inner diameters of at least one pair of bearings 86 which are provided on the slide frame 83. Furthermore, the bearing 86 is fitted to the shaft 87. This rotary frame 80 is rotated with respect to the slide frame 83 around this shaft 87 as a center. A rotation drive unit 89 for rotating the rotation frame 80 is constituted by a motor 89a fixed on the slide frame 83, a brake 89b, a pulley 88 fixed on a shaft end of this motor 89a, and also a detector 89c for detecting the rotation number of the motor 89a. While the pulley 88 fixed to the shaft 87 is coupled to the belt 90, the rotation drive force of this motor 89a is transferred to the rotation frame 80 so as to rotate the X-ray tube 2. As a result, the X-ray tube 2 may be variably set along an arbitrary direction.

Next, the drive apparatus for the X-ray image receiving apparatus 5 will now be described. In FIG. 5B, the X-ray image receiving apparatus 5 is fixed on a rotary frame 91. The rotary frame 91 is fitted to a slide frame 92 by way of a bearing 93 and a shaft 94. This slide frame 92 may slide the X-ray image receiving apparatus 5 on a straight line of the arm 72.

The arm 72 owns both a straight line guide unit 95 and an inner gear 96, at least one pair of rollers 97 are provided in the straight line guide unit 95 of the arm 72, and this roller 97 can slide the straight-line guide unit 95 of the arm 72 with respect to the slide frame 92.

A slide drive unit 98 which constitutes the above-described slide apparatus is arranged by a motor 98a fixed on the slide frame 92, a brake 98b, a gear 99 fixed on a shaft end of this motor 98a, and also a detector 98c for detecting a rotation number of the motor 98a. The X-ray image receiving apparatus 5 is slid/transported by meshing the gear 99 fixed on the shaft end with the inner gear 96 provided on the arm 72 to an opposite position against the X-ray tube 2.

The X-ray image receiving apparatus 5 is arranged in a direction opposite to the irradiation direction of the X-ray irradiated from the X-ray tube by rotating the rotary frame 91 by employing the below-mentioned mechanism.

In other words, the rotary frame 91 is fixed on one end of a shaft 94 having an outer diameter which is made substantially identical to inner diameters of at least one pair of bearings 93 which are provided on the slide frame 92. Furthermore, the bearing 93 is fitted to the shaft 94. This rotary frame 91 is rotated with respect to the slide frame 92 around this shaft 94 as a center. A rotation drive unit 100 for rotating the rotary frame 91 is constituted by a motor 100a fixed on the slide frame 92, a brake 100b, a pulley 101 fixed on a shaft end of this motor 100a, and also a detector 100c for detecting the rotation number of the motor 100a. While a pulley 101 fixed to the shaft 94 is coupled to a belt 102, the rotation drive force of this motor 100a is transferred to the rotary frame 91 so as to rotate the X-ray image receiving apparatus 5.

It should be understood that operations of the medical X-ray apparatus with employment of such a construction are substantially similar to the operations of the above-explained embodiment mode 1 except for such an operation that the fluoroscopic directions of the X-ray tube 2 and the X-ray image receiving apparatus 5 are variably changed.

That is to say, while the operation for sliding the straight-line guide unit shown in FIG. 4 is replaced by the curved-line guide unit shown in FIG. 1, an apparatus capable of variably changing the fluoroscopic directions of the X-ray tube 2 and the X-ray image receiving apparatus 5 is additionally provided and an arrangement of this control apparatus is represented in FIG. 6.

An operator instructs an operation device 30 to select any one of an X-ray fluoroscopic image and a cone-beam CT image in a similar manner to that of the embodiment mode 1. In response to this instruction, when the operator selects the function of acquiring the fluoroscopic image, an output of the X-ray image receiving apparatus 5 is entered into an image processing apparatus 40 by operating a switching device 36. In response to this instruction, when the operator selects the function of acquiring the cone-beam CT image, an output of the X-ray image receiving apparatus 5 is entered to another image processing apparatus 50 by operating the switching device 36.

C: In the Case that the Function of Acquiring the X-ray Fluoroscopic Image is Selected In such a case that the operator selects the function of acquiring the fluoroscopic image, a system controller 31 supplies a command to the switching device 36 by which the output of the X-ray image receiving apparatus 5 is entered into the image processing apparatus 40 for processing the fluoroscopic image data, and also supplies a control command to an X-ray tube slide control apparatus 33, an X-ray image receiving apparatus slide-control apparatus 32, a rotary plate control apparatus 34, an X-ray radiation direction control apparatus 100, and an X-ray image receiving direction control apparatus 111. This control command is used to position both the X-ray tube 2 and the X-ray image receiving apparatus 5 along a direction where the X-ray fluoroscopic operation is wanted to be carried out. The X-ray fluoroscopic operations according to the embodiment mode 2 of the present invention may be carried out by way of the below-mentioned methods along multiple directions in response to a diagnostic purpose and a curing purpose. Now, these operations will be explained as follows:

(C1) X-ray Fluoroscopie Operation Along Direction Perpendicular to Body Axis of Object Under Examination A control command is sent from the operation device 30 via the system controller 31 to both the X-ray radiation direction control apparatus 100 and the X-ray image receiving direction control apparatus 111. This control command may set the X-ray tube 2 and the X-ray image receiving apparatus 5 to such a position perpendicular to the body axis of the object under examination. In response to these direction control commands, the rotation angles of the X-ray tube 2 and the X-ray image receiving apparatus 5 are controlled by both the X-ray radiation direction control apparatus 100 and the X-ray image receiving direction control apparatus 111 in such a manner that both the X-ray tube 2 and the X-ray image receiving apparatus 5 are located perpendicular to the body axis of the object under examination.

These rotation angles are set to such rotation angles based upon the above-explained direction control command in such a manner that while the motors (89a and 100a) of the drive units 89 and 100 for rotating both the X-ray tube 2 and the X-ray image receiving apparatus 5 are rotated, the rotation force of the motors (89a and 100a) is transferred via the pulleys (88 and 101) provided on the shaft ends of these motors, and also via the belts (90 and 102) coupled to these pulleys to the rotation frame (80 and 91). As a result, both the X-ray tube 2 and the X-ray image receiving apparatus 5 are arranged opposite to each other perpendicular to the body axis of the object under examination.

Next, such a control command is transmitted via the system controller 31 to both the X-ray tube slide control apparatus 33 and the X-ray image receiving apparatus slide control apparatus 32. This control command instructs that the X-ray tube 2 is arranged opposite to the X-ray image receiving apparatus 5 at arbitrary positions on both the straight-line shaped arms 70 and 72, where the X-ray fluoroscopic operation is wanted to be carried out under such a condition that the rotation angles of the X-ray tube 2 and the X-ray image apparatus 5 are maintained at the above-described angles. In response to these slide position control commands, the motors (84a and 98a) of the drive units 84 and 98 for sliding the X-ray tube 2 and the X-ray image receiving apparatus 5 are rotated so as to rotate the gears (85 and 99) provided on the shaft ends of the motors. The slide frames 83 and 92 held under slidable condition are slid by the rollers (82 and 97) within the inner gears (81 and 96) which are meshed with these gears (85 and 99), so that both the X-ray tube 2 and the X-ray image receiving apparatus 5, which are supported by these slide frames (83 and 92), are arranged opposite to each other at such a position perpendicular to the body axis of the object under examination. In such a case that the X-ray tube 2 and the X-ray image receiving apparatus 5 are positioned to arbitrary rotation positions in order that the object under examination is treated by the X-ray fluoroscopic operation under this condition, or a traveling direction of a blood vessel is confirmed from another direction, an instruction is sent from the system controller 31 to the rotary plate rotation control apparatus 34 for controlling the rotation of the rotary plate 7 in response to an instruction of the operation device 30 operated by the operator in a manner similar to the above-described case. In response to this instruction, the drive unit 9 is driven so as to rotate the rotary plate 7. When the rotary plate 7 is reached to a target rotation angle position, the brake 9c is actuated so as to stop this rotary plate 7 at a desirable angle, so that both the X-ray tube 2 and the X-ray image receiving apparatus 5 are held under the stop condition. Then, the X-ray fluoroscopic operation is carried out with respect to the object under examination at this holding angle.

Then, both at the rotation angle position of the rotation plate 7 and in the slide positions of the X-ray tube 2 and the X-ray image receiving apparatus 5, the X-ray control apparatus 35 produces such an X-ray control amount used to generate X-rays corresponding to an X-ray condition supplied from the system controller 31 in response to an instruction issued from the operator by operating the operation device 30. The X-rays are generated by the X-ray tube 2 based upon the above-described control amount, and then, are irradiated to the object under examination. The X-rays which pass through this object under examination is entered into the X-ray image receiving apparatus 5 so as to be converted into an electric signal in an analog signal. This electric signal is processed by the image processing apparatus 40, so that a desirable X-ray fluoroscopic image may be represented on a display unit 60.

(C2) X-ray Fluoroscopic Operation from Direction Inclined with Respect to Body Axis of Object Under Examination First, an X-ray fluoroscopic operation with respect to an object under examination is determined based upon the following conditions: a) what position; b) what direction; and c) what angle around the object under examination.

Based upon the conditions, a position where the X-ray fluoroscopic operation is first carried out, namely both the X-ray tube 2 and the X-ray image receiving apparatus 5 are set to certain positions on the straight-line shaped arms 70 and 72. Next, at the above positions, a radiation direction of an X-ray is set. Namely, inclined angles (rotation angles) of the X-ray tube 2 and the X-ray image receiving apparatus 5 with respect to the body axis of the object under examination are set. Then, it is so determined that the X-ray fluoroscopic operation is carried out from which position around the object under examination (namely, rotation angle of rotary plate 7). Among these procedures, a description will now be made of such a case that the X-ray fluoroscopic operation is carried out along such a direction inclined to the body axis of the object under examination. The system controller 31 sends such a control command to both the X-ray tube slide control apparatus 33 and the X-ray image receiving apparatus slide control apparatus 32. Based upon this control command, both the X-ray tube 2 and the X-ray image receiving apparatus 5 are arranged opposite to each other at arbitrary positions on the straight-line shaped arms 70 and 72, where the X-ray fluoroscopic operation is wanted to be carried out. In response to this control command, both the X-ray tube 2 and the X-ray image receiving apparatus 5 are slid (namely, slide-transported by drive units 84 and 98), and then are stopped at the target positions.

Next, the system controller 31 sends such an inclination command to both the X-ray radiation direction control apparatus 100 and the X-ray image receiving direction control apparatus 111. This inclination command instructs that both the X-ray tube 2 and the X-ray image receiving apparatus 5 define an opposite angle at the above position with respect to the body axis of the object under examination. In response to this control command, both the X-ray tube 2 and the X-ray image receiving apparatus 5 are rotated (namely, rotated by drive units 89 and 100), and such an angle is set by which the X-ray tube 2 may be positioned opposite to the X-ray image receiving apparatus 5.

As a result, both the positions where the X-ray fluoroscopic operation is carried out and the inclination angles with respect to the body axis are set. While these positions and angles are arbitrarily set, the X-ray fluoroscopic operation can be carried out along the direction inclined with respect to the body axis.

In such a case that the X-ray tube 2 and the X-ray image receiving apparatus 5 are positioned to arbitrary rotation positions in order that a traveling direction of a blood vessel is confirmed from another direction, a rotation control instruction is sent from the operation device 30 to the rotary plate rotation control apparatus 34 for controlling the rotation of the rotary plate 7 so as to stop the rotary plate 7 at a desirable rotation position (rotated by drive unit 9). Then, this rotary plate 7 is held at this desirable rotation position where the X-ray fluoroscopic operation is carried out.

Then, an X-ray corresponding to the X-ray condition set by the operation device 30 is generated from the X-ray tube 2 to be irradiated to the object under examination. The X-ray which has penetrated through this object under examination is entered into the X-ray image receiving apparatus 5 so as to be converted into an electric signal. This electric signal is processed by the image processing apparatus 40, so that a desirable X-ray fluoroscopic image is displayed on the display unit 60.

D: In the Case that the Function of Acquiring the Cone-beam X-ray Image is Selected In such a case that the operator selects the function of acquiring the cone beam CT image, the system controller 31 supplies a command to the switching device 36 by which the output of the X-ray image receiving apparatus 5 is entered into the image processing apparatus 50 for processing the fluoroscopic image data, and also supplies such a control command to the X-ray tube slide control apparatus 33, the X-ray image receiving apparatus slide-control apparatus 32, the rotary plate rotation control apparatus 34, the X-ray radiation direction control apparatus 100, and the X-ray image receiving control apparatus 111.

The cone-beam CT imaging method according to the embodiment mode 2 of the present invention is carried out by the following methods. Subsequently, operations of these cone-beam CT imaging methods will now be explained.

(D1). In such a Case that Cone-beam CT Imaging Operation is Carried Out, While X-ray Tube 2 is Positioned Opposite to X-ray Image Receiving Apparatus 5 Perpendicular to Body Axis of Object Under Examination A control command is set from the operation device 30 via the system controller 31 to both the X-ray radiation direction control apparatus 100 and the X-ray image receiving direction control apparatus 111. This control command may set both the X-ray tube 2 and the X-ray image receiving apparatus 5 to such a position perpendicular to the body axis of the object under examination. Namely, the rotations of the X-ray tube 2 and the X-ray image receiving apparatus 5 are controlled by the drive units 89 and 100. As a result, both the X-ray tube 2 and the X-ray image receiving apparatus 5 are arranged opposite to each other perpendicular to the body axis of the object under examination.

Next, such a control command is transmitted via the system controller 31 to both the X-ray tube slide control apparatus 33 and the X-ray image receiving apparatus slide control apparatus 32. This control command instructs that the X-ray tube 2 is arranged opposite to the X-ray image receiving apparatus 5 at arbitrary positions on both the line-line shaped arms 70 and 72, where the X-ray fluoroscopic operation is wanted to be carried out under such a condition that the rotation angles of the X-ray tube 2 and the X-ray image apparatus 5 are maintained at the above-described angles. Based upon these slide position control commands, the drive units 84 and 98 for sliding both the X-ray tube 2 and the X-ray image receiving apparatus 5 slide the slide frames (83 and 91), so that both the X-ray tube 2 and the X-ray image receiving apparatus 5 supported on these slide frames (83 and 91) are stopped and held at such a position corresponding to the above-explained control position instruction. At a stage where a preparation for positioning of the object under examination is completed, the operator manipulates the operation device 30 so as to supply a rotation control command to the rotary plate rotation control apparatus 34 by the system controller 31 in order that the cone-beam CT image is photographed. In response to this rotation control command, the motor 9a of the drive unit 9 is rotated to rotate the rotary plate 7.

At such a time instant when the rotation speed of the rotary plate 7 is reached to a constant rotation speed, the system controller 31 controls the X-ray tube 2 via the X-ray control apparatus 35 to radiate X-rays. Then, the X-ray image receiving apparatus 5 detects X-rays which have passed through the object under examination while the rotary plate 7 is rotated by 1 turn, and then converts these detected X-rays into an electric signal.

The signal detected by the X-ray image receiving apparatus 5 is processed by the image processing apparatus 50 in a similar processing manner to that of the above-explained case (B1). Then, the produced three-dimensional image is displayed on the display device 60.

In accordance with this method, a three-dimensional image may be acquired. That is, this three-dimensional image owns a certain width of a sectional plane perpendicular to the body axis of the object under examination.

(D2): In the Case that Cone-beam CT Image is Acquired While Both X-ray Tube 2 and X-ray Image Receiving Apparatus 5 are Inclined with Respect to Body Axis of Object Under Examination First, a cone-beam X-ray CT image acquiring operation with respect to an object under examination is determined based upon the following conditions: a) what position; and b) what direction.

Based upon the conditions, first, both the X-ray tube 2 and the X-ray image receiving apparatus 5 are set to certain positions on the straight-line shaped arms 70 and 72. Next, at the above positions, a radiation direction of an X-ray is set. Namely, inclined angles (rotation angles) of the X-ray tube 2 and the X-ray image receiving apparatus 5 with respect to the body axis respect to the body axis of the object under examination are set. Then, the rotary plate 7 is rotated to acquire a cone-beam CT image of the object under examination. A description will now be made of such a case that a cone-beam CT image is acquired along such a direction inclined to the body axis of the object under examination based upon these procedures.

The system controller 31 sends such a control command to both the X-ray tube slide control apparatus 33 and the X-ray image receiving apparatus slide control apparatus 32. Based upon this control command, both the X-ray tube 2 and the X-ray image receiving apparatus 5 are arranged opposite to each other at arbitrary positions on the straight-line shaped arms 70 and 72. In response to this control command, both the X-ray tube 2 and the X-ray image receiving apparatus 5 are slid (namely, slide-transported by drive units 84 and 98), and then are stopped at the target positions.

Next, the system controller 31 sends such an inclination command to both the X-ray radiation direction control apparatus 100 and the X-ray image receiving direction control apparatus 111. This inclination command instructs that both the X-ray tube 2 and the X-ray image receiving apparatus 5 define an opposite angle at the above position with respect to the body axis of the object under examination. In response to this control command, both the X-ray tube 2 and the X-ray image receiving apparatus 5 are rotated (namely, rotated by drive units 89 and 100), and such an angle is set by which the X-ray tube 2 may be positioned opposite to the X-ray image receiving apparatus 5.

At a stage where a preparation for positioning of the object under examination is completed based upon such a procedure, the operator manipulates the operation device 30 so as to supply a rotation control command to the rotary plate rotation control apparatus 34 by the system controller 31 in order that the cone-beam CT image is photographed. In response to this rotation control command, the motor 9*a* of the drive unit 9 is rotated to rotate the rotary plate 7.

At such a time instant when the rotation speed of the rotary plate 7 is reached to a constant rotation speed, the system controller 31 controls the X-ray tube 2 via the X-ray control apparatus 35 to radiate X-rays. Then, the X-ray image receiving apparatus 5 detects X-rays which have passed through the object under examination while the rotary plate 7 is rotated by 1 turn, and then converts this detection signal into an electric signal. Then, this electric detection signal is entered into the image processing apparatus 50 so as to perform various sorts of image processing operations, so that a desirable three-dimensional image is displayed on the display unit 60.

In accordance with this method, a three-dimensional image may be acquired. That is, this three-dimensional image owns a certain width of a sectional plane perpendicular to the body axis of the object under examination.

(D3). In Such a Case that While X-ray Tube 2 and X-ray Image Receiving Apparatus 5 are Slid Along Reverse Directions Under Condition that Both X-ray Tube 2 and X-ray Image Receiving Apparatus 5 Maintain Opposite Positional Relationship, Rotary Plate 7 is Rotated to Photograph Cone-beam X-ray CT Image While the X-ray image receiving apparatus 5 and the X-ray tube 2 are operated under control of the X-ray tube slide control apparatus 33 and the X-ray image receiving apparatus slide control apparatus 32, the rotary plate 7 is rotated so as to acquire a cone-beam X-ray CT image under such a condition that the opposite positional relationship between the X-ray tube 2 and the X-ray image receiving apparatus 5 is maintained, and also this X-ray tube 2 and the X-ray image receiving apparatus 5 are slid along the reverse directions.

For instance, while the X-ray tube 2 is arranged at a position "c1" of the right end of FIG. 4 and also the X-ray image receiving apparatus 5 is arranged at another position "d1" of the left end of FIG. 4, both the X-ray tube 2 and the X-ray image receiving apparatus 5 are mutually moved along the reverse directions by rotating the rotary plate 7 under such a condition that the opposite positional relationship between the X-ray tube 2 and the X-ray image receiving apparatus 5 is maintained in such a manner that the X-ray tube 2 is moved from the above position "c1" up to another position "c2", and the X-ray image receiving apparatus 5 is moved from the above position "d1" up to another position "d2."

In this cone-beam X-ray CT image operation, the rotation angles of both the X-ray tube 2 and the X-ray image receiving apparatus 5 must be controlled by employing both the X-ray radiation direction control apparatus 100 and the X-ray image direction control apparatus 111 in such a manner that even when both the X-ray tube and the X-ray image receiving apparatus 5 are located at any positions on the straight-line shaped arms 70 and 72, the opposition positional relationship between them can be maintained. In accordance with this method, since the image data can be acquired along the omnidirection by projecting the X-rays only one time without moving the object under examination, such a three-dimensional image corresponding to the multiple directions can be produced within one time by processing the acquired image data by the image processing unit 50. Then, this three-dimensional image can be indicated on the display unit.

(D4). In Such a Case that Under Such a Condition that X-ray Tube 2 and X-ray Image Receiving Apparatus 5 Maintain Opposite Positional Relationship, Cone-beam X-ray CT Image is Acquired While the X-ray Tube 2 and the X-ray Image Acquiring Unit 5 are Transported Along Same Direction at the Same Time Under control of the X-ray radiation direction control apparatus 100 and the X-ray image receiving control apparatus 111, both the X-ray tube 2 and the X-ray image receiving apparatus 5 are arranged opposite to each other and also positioned perpendicular to the body axis of the object under examination. While maintaining this condition, both the X-ray tube 2 and the X-ray image receiving apparatus 5 are transported over the straight-line shaped arms 70 and 72 at the same time, and the rotary plate 7 is continuously rotated so as to acquire a cone-beam X-ray CT image. For instance, while the X-ray tube 2 is arranged at a position "c1" of the right end of FIG. 4 and also the X-ray image receiving apparatus 5 is arranged at another position "d2" of the right end of FIG. 4, both the X-ray tube 2 and the X-ray image receiving apparatus 5 are mutually transported along the same direction by rotating the rotary plate 7 under such a condition that the opposite positional relationship between the X-ray tube 2 and the X-ray image receiving apparatus 5 is maintained in such a manner that the X-ray tube 2 is moved from the above position "c1" up to another position "c2", and the X-ray image receiving apparatus 5 is moved from the above position "d2" up to another position "d1", by rotating the rotary plate 7. In accordance with this method, since the image data can be acquired along the omnidirection by projecting the X-rays only one time, such a three-dimensional image over a wide range can be produced within one time.

(D5) Other Imaging Methods

Under such a condition that both the X-ray tube 2 and the X-ray image receiving apparatus 5 are arranged opposite to each other at arbitrary positions on the straight-line arms 70 and 72 and then are brought into stational states, a cone-beam X-ray CT imaging operation may be carried out, while the rotary plate 7 is rotated and a table 202 for mounting thereon the object 201 under examination is transported. In accordance with this imaging method, since such three-dimensional images of the object 201 under examination over a wide range can be acquired within one time, the positional relationship between a curing portion and a portion adjacent to this curing portion can be made clear, so that the entire portion of the object under examination can be effectively grasped.

Similar to the above-described embodiment mode 1, the medical X-ray apparatus of this embodiment mode 2 of the present invention is suitable for the IVR method.

In the case that this medical X-ray apparatus of the embodiment mode 2 is employed in the IVR in order to three-dimensionally grasp a position of a target portion and a shape of this target portion prior to the curing operation, the cone-beam CT imaging method is selected to produce a three-dimensional image of this target portion, and this three-dimensional image is displayed on the display unit. In this case, this cone-beam X-ray CT imaging method is suitable for the curing methods as explained in the above-explained (D1) to (D5).

Similar to the embodiment mode 1, as a representation of the above-explained cone-beam CT image, there are the below-mentioned display methods: That is to say, (a). The three-dimensional images produced by the methods explained in the above-described items (D1) to (D5) are separately displayed.

(b). At least two sets of the three-dimensional images produced by the methods explained in the above-explained items (D1) to (D5) are displayed at the same time. For example, both the image photographed by that the X-ray tube 2 and the X-ray image receiving apparatus 5 are arranged opposite to each other perpendicular to the body axis of the object under examination (see item D1), and the image photographed by that the X-ray tube 2 and the X-ray image receiving apparatus 5 are inclined with respect to the body axis of the object under examination (see item D2) are displayed at the same time. Alternatively, either the image explained in the item (D1) or the image explained in the item (D2), and another image explained in the item (D3) are displayed at the same time. That is, as to the image of the item (D3), under such a condition that the opposite positional relationship between the X-ray tube 2 and the X-ray image receiving apparatus 5 is maintained, the rotary plate 7 is rotated to acquire the image, while the X-ray tube 2 and the X-ray image receiving apparatus 5 are slid along the reverse directions.

(c). These images may be displayed on the same display unit, or on different display units. Also, this simultaneous image display is not limited to two sorts of images, but more than two sorts of images may be displayed.

The traveling conditions of the blood vessels mixed with each other in complex manners are three-dimensionally observed based upon the images which are produced and displayed in this manner. Based upon this result, the catheter is manipulated to perform the dilating operation of the blood vessel under condition of infarction, while observing the fluoroscopic images acquired by the methods of the above-explained items (C1) and (C2) of the embodiment mode 2. While this curing operation is carried out, the fluoroscopic images produced by the methods explained in the items (C1) and (C2) are solely displayed. In addition, both the fluoroscopic image acquired from the direction perpendicular to the body axis of the object under examination, and the fluoroscopic image acquired from the direction inclined to the body axis of the object under examination are displayed on either the same monitor, or the separate monitors. While referring to both the images displaying an arbitrary three-dimensional image selected from the above-explained cone-beam CT images and also the above-described fluoroscopic images are displayed on either the same display unit, or the separate display units, the operator can advance the curing operation by using these images as the guide purpose. Thereafter, after the curing operation is accomplished, the operator selects the cone-beam CT image so as to acquire a three-dimensional image, and then, can confirm the curing effects based upon this acquired three-dimensional image.

As previously described, in accordance with the embodiment mode 2 of FIG. 4, in addition to a similar effect to that of the embodiment mode 1 shown in FIG. 1, since the shapes of the arms which may support both the X-ray tube 2 and the X-ray image receiving apparatus 5 are made in such straight-line forms, there are the following effects. That is, the slide mechanisms used for the X-ray tube 2 and the X-ray image receiving apparatus 5 can be made simple. Also, these supporting arms can be readily manufactured, and the rotary plates can be easily fixed on these arms.

Figure 7:
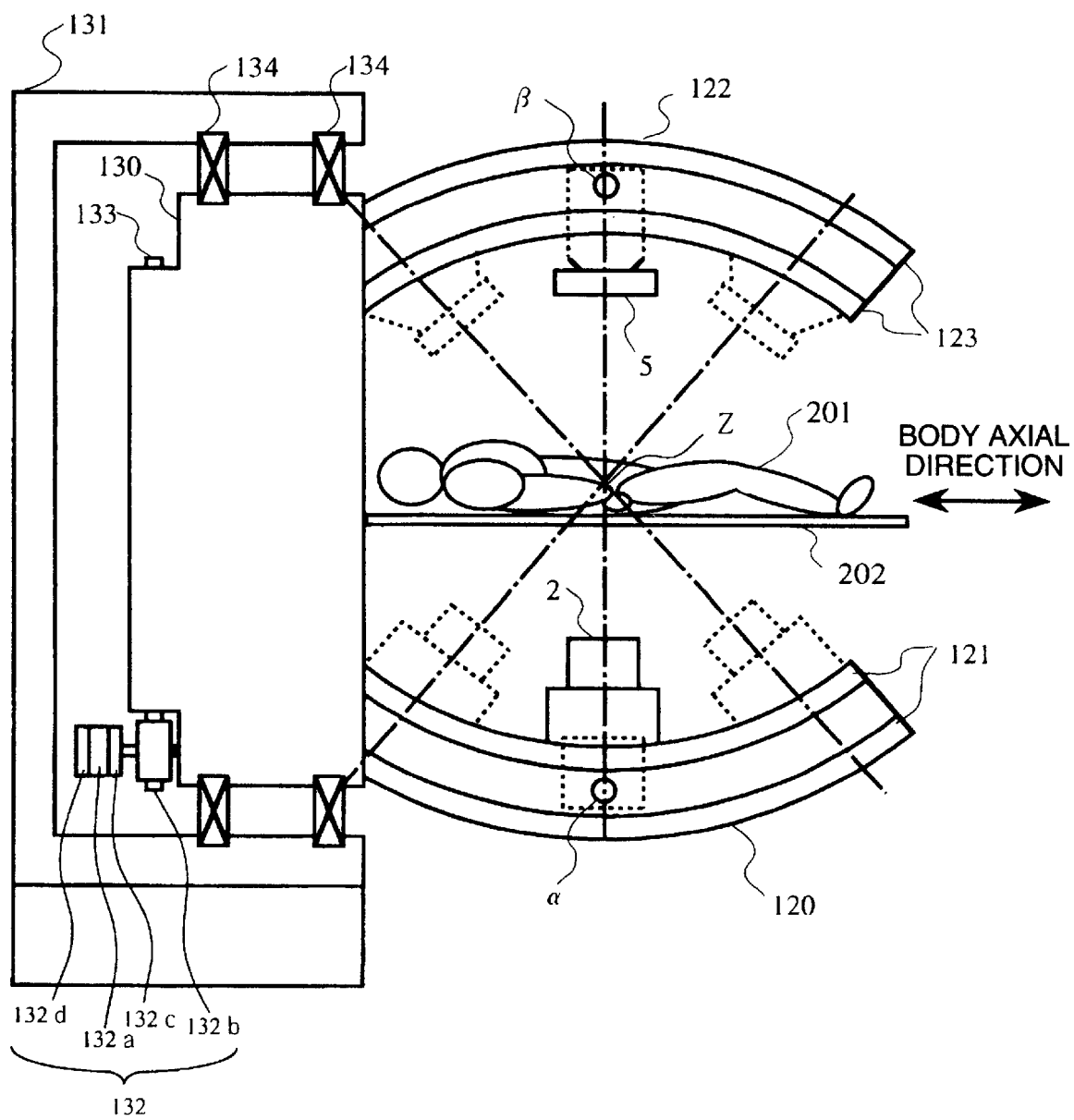
FIG. 7 is a schematic diagram for showing a construction of a medical X-ray apparatus according to an embodiment mode 3 of the present invention.

FIG. 7 is a structural diagram for representing a medical X-ray apparatus according to an embodiment mode 3 of the present invention.

The medical X-ray apparatus, according to this embodiment mode 3 of the present invention, is arranged by that the opening portion of the embodiment mode 1 shown in FIG. 1, into which the object under examination is inserted, is omitted from the medical X-ray apparatus of the embodiment mode 1.

In FIG. 7, reference numeral 120 indicates an arc-shaped arm. The arc-shaped arm 120 supports an X-ray tube 2 for irradiating an X-ray to an object 201 under medical examination, and is fixed on a rotary plate 130. The X-ray tube 2 is arranged in such a manner that this X-ray tube 2 may be transported by a curved-line guide unit 121 over the arm 120 within a curvature plane where an iso-center "Z" is located as a center thereof.

Reference numeral 122 shows an arc-shaped arm fixed on the rotary plate 130. The arc-shaped arm 122 supports an X-ray image receiving apparatus 5. The X-ray image receiving apparatus 5 is arranged at a position opposite to the X-ray tube 2 with sandwiching the object under examination, and detects an X-ray which is penetrated through the object under examination so as to convert the detected X-ray into an electric signal. The X-ray image receiving apparatus 5 is arranged in such a manner that this X-ray image receiving apparatus 5 may be transported by a curved-line guide unit 123 over the arm 122 within a curvature plane having the iso-center "Z" as a center thereof, while this X-ray image receiving apparatus 5 is located opposite to the X-ray tube 2. The above-described X-ray apparatus 5 is construct of both an image intensifier and a television camera, or both the image intensifier and a CCD (change-coupled device) camera. Alternatively, a flat panel type two-dimensional sensor using a semiconductor detector may employed as the X-ray image receiving apparatus.

The rotary plate 130 is ratably supported via at least one pair of bearings 134 with respect to a supporting frame 131 for supporting this rotary plate. Rotation drive force derived from a drive unit 132 is transferred via a belt 133 to the bearings 134 so as to rotate the rotary plate 130. The drive unit 132 is constituted by a motor 132a fixed on the supporting frame 131, a pulley 132b fixed on the motor shaft of this motor 132a, a brake 132c used to stop rotations of the motor 132a, and a detector 132d for detecting a rotation number of the motor 132a. The detector 132d detects the actual rotation number of the motor 132a, and then, the detection value is employed so as to control the rotary plate 131 at a predetermined rotation number (control apparatus is omitted). Since the medical X-ray apparatus is arranged in the above-explained manner, both the arm 120 and the arm 122, which are fixed on the rotary plate 130 can be rotated around an axial line as a center. This axial line is located parallel to the body axial direction involving the iso-center "Z", and further, both the X-ray image receiving apparatus 5 and the X-ray rube 2 are rotatable, while the X-ray image receiving apparatus 5 is located opposite to the X-ray tube 2. As previously described, in this embodiment mode 3 of the present invention, the opening portions into which the object under examination is not provided with the rotary plate 130 and also the supporting frame 131 for rotatably supporting this rotary plate 130. It should be understood that since the lengths of the above-explained arc-shaped arms 120 and 122 are selected to be longer than, or equal to 1 meter, and shorter than, or equal to 2 meters, this medical X-ray apparatus may accept the entire portion of this object under examination.

Since transport apparatus for slide-transporting the X-ray tube 2 and the X-ray image receiving apparatus 5 over the respective arc-shaped arms are the same as those of the embodiment mode 1 shown in FIG. 2A and FIG. 2B, explanations thereof are omitted.

In accordance with this embodiment mode 3, while an object 201 under examination is set on a table 202 with having a proper attitude corresponding to a diagnostic purpose and a curing purpose, this table 202 is arranged on the horizontal axial line of the iso-center "Z." Then, both an X-ray fluoroscopic image and a cone-beam CT image are produced. While observing these images, an operator may perform a diagnostic treatment and a curing operation.

In accordance with this embodiment mode 3, in addition to a similar effect to that achieved by the above-explained embodiment mode 1, since the length of the arms 120 and 122 are made in correspondence with the height of the object under examination, there is such an effect that while the object under examination is not moved, both the X-ray fluoroscopic image and the cone-beam CT image can be produced.

Figure 8:
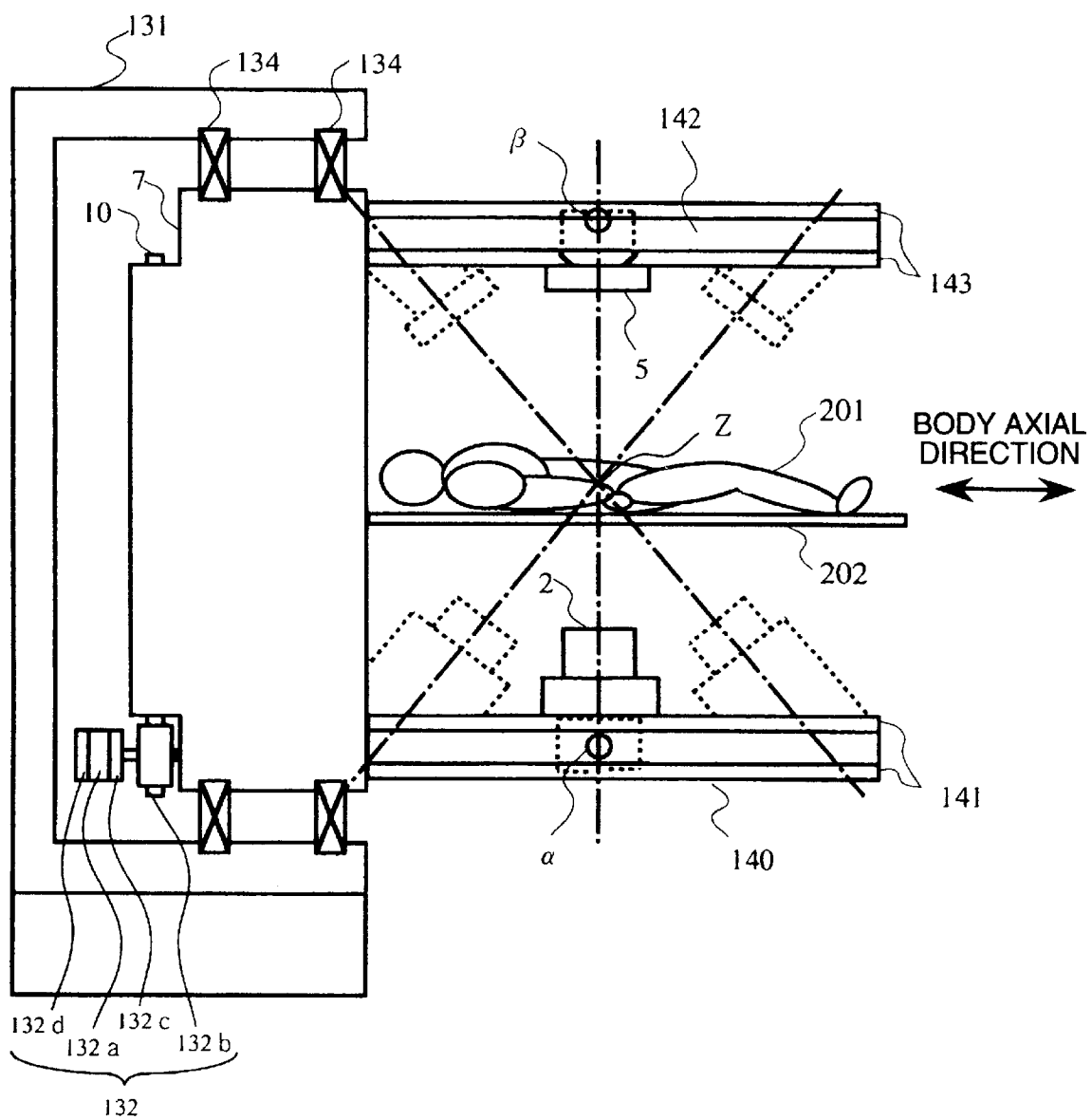
FIG. 8 is a schematic diagram for showing a construction of a medical X-ray apparatus according to an embodiment mode 4 of the present invention.

FIG. 8 is a structural diagram for representing a medical X-ray apparatus according to an embodiment mode 4 of the present invention.

The medical X-ray apparatus, according to this embodiment mode 4 of the present invention, is arranged by that the opening portion of the embodiment mode 4 shown in FIG. 4, into which the object under examination is inserted, is omitted from the medical X-ray apparatus of the embodiment mode 2.

In FIG. 8, reference numeral 140 indicates a straight-line shaped arm. The straight-line shaped arm 140 supports an X-ray tube 2 for irradiating an X-ray to an object 201 under medical examination. The X-ray tube 2 is arranged in such a manner that this X-ray tube 2 may be transported by a straight-line guide unit 141 over the arm 140 in a linear manner.

Reference numeral 142 shows a straight-line shaped arm fixed on the rotary plate 130. The straight-line shaped arm 142 supports an X-ray image receiving apparatus 5. The X-ray image receiving apparatus 5 is arranged at a position opposite to the X-ray tube 2 with sandwiching the object under examination, and detects an X-ray which is penetrated through the object under examination so as to convert the detected X-ray into an electric signal. The X-ray image receiving apparatus 5 is arranged in such a manner that this X-ray image receiving apparatus 5 may be transported by a straight-line guide unit 142 over the arm 142 in a linear manner. The above-described X-ray apparatus 5 is constructed of both an image intensifier and a television camera, or both the image intensifier and a CCD (charge-coupled device) camera. Alternatively, a flat panel type two-dimensional sensor using a semiconductor detector may employed as the X-ray image receiving apparatus.

Since supporting of the rotary plate 130 and rotation-driving of this rotary plate 130 are the same as those of the above-explained embodiment mode 3 shown in FIG. 7, descriptions of this construction are omitted. Since such a construction is employed, both the arm 140 and the arm 142 which are fixed on the rotary plate 131 can be rotated around such an axial line horizontally located with respect to the body axis containing the iso-center "Z", so that the X-ray image receiving apparatus 5 and the X-ray tube 2 can be rotated while being located opposite to each other.

As previously described, in this embodiment mode 4 of the present invention, the opening portions into which the object under examination is not provided with the rotary plate 130 and also the supporting frame 131 for rotatably supporting this rotary plate 130. It should be understood that since the lengths of the above-explained straight-line shaped arms 140 and 142 are selected to be longer than, or equal to 1 meter, and shorter than, or equal to 2 meters, this medical X-ray apparatus may accept the entire portion of this object under examination.

Since transport apparatus for slide-transporting the X-ray tube 2 and the X-ray image receiving apparatus 5 over the respective straight-line shaped arms are the same as those of the embodiment mode 2 shown in FIG. 5A and FIG. 5B, explanations thereof are omitted.

Also, in accordance with this embodiment mode 4, while an object 201 under examination is set on a table 202 with having a proper attitude corresponding to a diagnostic purpose and a curing purpose, this table 202 is arranged on the horizontal axial line of the iso-center "Z." Then, both an X-ray fluoroscopic image and a cone-beam CT image are produced. While observing these images, an operator may perform a diagnostic treatment and a curing operation.

In accordance with this embodiment mode 4, in addition to a similar effect to that achieved by the above-explained embodiment mode 2, since the length of the arms 140 and 142 are made in correspondence with the height of the object under examination, there is such an effect that while the object under examination is not moved, both the X-ray fluoroscopic image and the cone-beam CT image can be produced.

In the above-described embodiment modes 1 to 4, both the rotary plate and the object under examination are brought into the stationary conditions, and both the X-ray tube 2 and the X-ray image receiving apparatus 5 are mutually transported along the reverse directions, while the opposite positional relationship between the X-ray tube 2 and the X-ray image receiving apparatus 5 is maintained, during which the object under examination is photographed. As a result, the tomographic imaging operation of the plane which is located in parallel to the body axis of the object under examination can be carried.

As this tomographic imaging operation, there are two methods, namely a method (Tomography) in which both the X-ray tube 2 and the X-ray image receiving apparatus 5 are moved in an arc manner in a symmetric mode, while the iso-center "Z" is used as a fulcrum; and also, another method (Planigraphy) in which both the X-ray tube 2 and the X-ray image receiving apparatus 5 are moved in a linear fashion in a symmetrical manner, while the iso-center "Z" is employed as a fulcrum ("MEDICAL IMAGE/RADIOGRAM APPLIANCE HANDBOOK" issued on Mar. 10, 1988, on page 110, FIG. 2.12-2, Denshi Keisoku Publisher, edited by Japanese Radiogram Appliance Industrial Group). In the embodiment modes 1 to 4 of the present invention, the above-explained tomographic imaging operations may be carried out.

Subsequently, a description will now be made of such a case that this temographic imaging operaiton is carried out.

(1) A method (Tomography) in which both X-ray tube 2 and X-ray image receiving apparatus 5 are moved in an arc manner, while the iso-center "Z" is employed as a fulcrum:

This method may be carried out in the embodiment modes of FIG. 1 and FIG. 7.

In these embodiment modes, while an imaging portion is focused onto the iso-center "Z", the X-ray tube 2 and the X-ray image receiving apparatus 5 are arranged opposite to each other along reverse directions. For instance, the X-ray tube 2 is arranged on a right end whereas the X-ray image receiving apparatus 5 is arranged on a left end. While the X-ray tube 2 and the X-ray image receiving apparatus 5 are mutually slid along the reverse directions with maintaining the opposite positional relationship between them, the tomographic imaging operation is carried out. As a result, an output of the X-ray image receiving apparatus 5 is processed by the image processing apparatus 50, so that a tomographic image of a plane which is located in parallel to the body axis of the object under examination may be acquired.

(2) A method (planigraphy) in which both X-ray tube 2 and X-ray image receiving apparatus 5 are linearly moved in a symmetric manner, while the isocenter "Z" is employed as a fulcrum:

This method may be carried out in the embodiment modes of FIG. 2 and FIG. 8.

In these embodiment modes, while an imaging portion is focused onto the iso-center "Z", the X-ray tube 2 and the X-ray image receiving apparatus 5 are arranged opposite to each other along reverse directions. For instance, the X-ray tube 2 is arranged on a right end whereas the X-ray image receiving apparatus 5 is arranged on a left end. While the X-ray tube 2 and the X-ray image receiving apparatus 5 are mutually slid along the reverse directions with maintaining the opposite positional relationship between them, the tomographic imaging operation is carried out. As a result, an output of the X-ray image receiving apparatus 5 is processed by the image processing apparatus 50, so that a planigraphic image of a plane which is located in parallel to the body axis of the object under examination may be acquired.

As previously explained, in the embodiment mode 5, since the tomographic image of such a plane which is located in parallel to the body axis of the object under examination may be obtained, both the positional information and the shape information as to the portion which should be diagnosed and cured may become rich in combination with the above-explained X-ray fluoroscopic image and cone-beam CT image, which could contribute improvements in operabilities of the diagnostic operations and also the curing operations.

It should also be noted that in the above-explained embodiment mode 1 to 4, both the rotary plate and the supporting frame for supporting this rotary plate are fixed, to which the present invention is not limited. Alternatively, while such apparatus capable of transporting the rotary plate and the supporting frame are provided with these rotary plate and supporting frame, the object under examination is fixed, and further, both the rotary plate and the supporting frame may be transported so as to carry out imaging operations.

It should also be understood that the present invention is not limited to the above-described respective embodiments, but may cover various modification examples defined by the claims for a patent.

What is claimed is:

1. A medical X-ray apparatus comprising:
   a supporting frame;
   a rotary member rotatably supported by said supporting frame;
   a rotation control apparatus for controlling a rotation of said rotary member;
   a first supporting member supported by said rotary member, for supporting an X-ray tube apparatus which irradiates an X-ray to an object under examination;
   a second supporting member for supporting a detection apparatus for detecting a transmission X-ray of said object under examination, said second supporting member being supported by said rotary member and being arranged opposite to said X-ray tube apparatus;
   a control apparatus for setting an irradiation angle of said X-ray substantially along a body axial direction of said object under examination to an arbitrary irradiation angle, and also for arranging said detection apparatus to axially oppose said X-ray tube apparatus in correspondence with said set arbitrary irradiation angle;
   an image processing apparatus for processing an output signal from said detection apparatus so as to produce both a two-dimensional image and a three-dimensional image; and
   a display apparatus for displaying the image produced by said image processing apparatus.

2. A medical X-ray apparatus as claimed in claim 1 wherein:

said supporting frame owns an opening portion used to insert a table for mounting thereon said object under examination along a horizontal direction; and said rotating member is rotated around said opening portion.

3. A medical X-ray apparatus as claimed in claim 1 wherein:

said control apparatus is comprised of:
  a first transporting apparatus for transporting said X-ray tube apparatus to an arbitrary position on said first supporting member; and
  a second transporting apparatus for transporting said detection apparatus to an arbitrary position on said second supporting member.

4. A medical X-ray apparatus as claimed in claim 3 wherein:

said control apparatus is further comprised of:
  an irradiation angle control apparatus for setting the irradiation angle of said X-ray tube apparatus to an arbitrary irradiation angle; and
  a detection apparatus angle control apparatus for controlling that the angle of said detection apparatus is located opposite to said X-ray tube apparatus in response to said set irradiation angle.

5. A medical X-ray apparatus as claimed in claim 1 wherein:

said medical X-ray apparatus is comprised of said first and second supporting members which are formed in an arc shape.

6. A medical X-ray apparatus as claimed in claim 1 wherein:

said medical X-ray apparatus is comprised of said first and second supporting members which are formed in a straight-line shape.

7. A medical X-ray apparatus as claimed in claim 1, wherein said image processing apparatus comprises a first image processing apparatus for reconstructing a tomographic image from said output signal from said detection apparatus, said output signal being obtained by irradiating an X-ray to said object under examination while said X-ray tube apparatus and said detection apparatus are rotated around said object under examination by rotating said rotary member.

8. A medical X-ray apparatus as claimed in claim 7, wherein said X-ray tube apparatus and said detection apparatus are inclined with respect to a body axis of said object under examination.

9. A medical X-ray apparatus as claimed in claim 7, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

10. A medical X-ray apparatus as claimed in claim 7, wherein said rotary member is rotated while said X-ray tube apparatus and said detection apparatus are respectively slid along said first and second supporting members under condition that said X-ray tube apparatus and said detection apparatus to maintain an opposite positional relationship.

11. A medical X-ray apparatus as claimed in claim 7, wherein said rotary member is rotated while a table on which said object under examination is lying is moved in said body axial direction.

12. A medical X-ray apparatus as claimed in claim 1, wherein said image processing apparatus comprises a second image processing apparatus for executing an image processing to X-ray data obtained in an X-ray fluoroscopic operation.

13. A medical X-ray apparatus as claimed in claim 12, wherein said image processing apparatus comprises a switching device for switching said first and second image processing apparatuses.

14. A medical X-ray apparatus as claimed in claim 12, wherein said X-ray fluoroscopic operation is executed while a table on which said object under examination is lying is moved in said body axial direction.

15. A medical X-ray apparatus as claimed in claim 1, wherein said image processing apparatus comprises a first image processing apparatus for reconstructing a tomographic image from said output signal from said detection apparatus, said output signal being obtained by irradiating an X-ray to said object under examination while said X-ray tube apparatus and said detection apparatus are rotated around said object under examination by rotating said rotary member, and said image processing apparatus comprises a second image processing apparatus for executing an image processing to X-ray data obtained in an X-ray fluoroscopic operation.

16. A medical X-ray apparatus as claimed in claim 15, wherein said image processing apparatus comprises a switching device for switching said first and second image processing apparatuses.

17. A medical X-ray apparatus as claimed in claim 1, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

18. A medical X-ray apparatus comprising:

a supporting frame;

a rotary member rotatably supported by said supporting frame;

a rotation control apparatus for controlling a rotation of said rotary member;

a first supporting member supported by said rotary member, for supporting an X-ray tube apparatus which irradiates an X-ray to an object under examination;

a second supporting member for supporting a detection apparatus for detecting a transmission X-ray of said object under examination, said second supporting member being supported by said rotary member and being arranged opposite to said X-ray tube apparatus;

an X-ray tube apparatus transporting apparatus for transporting said X-ray tube apparatus to an arbitrary position on said first supporting member;

a detection apparatus transporting apparatus for transporting said detection apparatus to an arbitrary position on said second supporting member;

a control apparatus for setting an irradiation angle of an X-ray substantially along a body axial direction of said object under examination to an arbitrary irradiation angle, and also for arranging said detection apparatus to axially oppose said X-ray tube apparatus in correspondence with said set arbitrary irradiation angle;

an image processing apparatus for processing an output signal from said detection apparatus so as to produce both a two-dimensional image and a three-dimensional image; and a display apparatus for displaying the image produced by said image processing apparatus.

19. A medical X-ray apparatus as claimed in claim 18, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

20. A medical X-ray apparatus comprising:
   a supporting frame;
   a rotary member rotatably supported by said supporting frame;
   a rotation control apparatus for controlling a rotation of said rotary member;
   a first supporting member whose one end is supported at a first position of said rotary member, and which is elongated along a body axial direction of an object under examination;
   an X-ray tube apparatus movably supported on said first supporting member, for irradiating an X-ray to said object under examination;
   a second supporting member whose one end is supported at a second position of said rotary member, and which is elongated along the body axial direction of said object under examination;
   a detection apparatus movably supported on said second supporting member, for detecting an X-ray penetrated through said object under examination, which is arranged opposite to said X-ray tube apparatus while sandwiching said object under examination;
   a control apparatus for setting an irradiation angle of an X-ray substantially along said body axial direction of said object under examination to an arbitrary irradiation angle, and also for arranging said detection apparatus to axially oppose said X-ray tube apparatus in correspondence with said arbitrary irradiation angle set;
   an image processing apparatus for processing an output signal from said detection apparatus so as to produce both a two-dimensional image and a three-dimensional image; and
   a display apparatus for displaying the image produced by said image processing apparatus.

21. A medical X-ray apparatus as claimed in claim 20, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

22. A medical X-ray apparatus comprising:
   a supporting frame having an opening portion used to insert a table for mounting an object under examination thereon along a horizontal direction;
   a rotary member rotatably supported by said supporting frame, said rotary member being able to rotate around said opening portion;
   a rotation control apparatus for controlling a rotation of said rotary member;
   a first arc-shaped supporting member whose one end is supported at a first position of said rotary member, and which is elongated along a body axial direction of an object under examination;
   an X-ray tube apparatus movably supported on said first arc-shaped supporting member, for irradiating an X-ray to said object under examination;
   a second arc-shaped supporting member whose one end is supported at a second position of said rotary member, and which is elongated along the body axial direction of said object under examination;
   a detection apparatus movably supported on said second arc-shaped supporting member for detecting an X-ray penetrated through said object under examination, which is arranged opposite to said X-ray tube apparatus while sandwiching said object under examination;
   an X-ray tube transporting apparatus for transporting said X-ray tube apparatus to an arbitrary position on said first arc-shaped supporting member;
   a detection transporting apparatus for transporting said detection apparatus to an arbitrary position on said second arc-shaped supporting member;
   a control apparatus for setting an irradiation angle of an X-ray substantially along said body axial direction of said object under examination to an arbitrary irradiation angle, and also for arranging said detection apparatus to axially oppose said X-ray tube apparatus in correspondence with said arbitrary irradiation angle;
   a first image processing apparatus for producing a three-dimensional image from a first output signal from said detection apparatus, said first output signal being obtained by irradiating an X-ray to said object in a first case that said rotary member is rotated under condition that said X-ray tube apparatus and said detection apparatus maintain an axially opposing positional relationship and/or said X-ray tube apparatus and said detection apparatus are respectively slid along said first and second arc-shaped supporting members under condition that said X-ray tube apparatus and said detection apparatus maintain an axially opposing positional relationship or in a second case that said rotary member is rotated under condition that said X-ray tube apparatus and said detection apparatus maintain an axially opposing positional relationship while said table is moved in said body axial direction;
   a second image processing apparatus for producing a two-dimensional image from a second output signal from said detection apparatus, said second output signal being obtained by irradiating an X-ray to said object under examination in an X-ray fluoroscopic operation; and
   a display apparatus for displaying the image produced by said image processing apparatus.

23. A medical X-ray apparatus as claimed in claim 22, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

24. A medical X-ray apparatus comprising:
   a supporting frame having an opening portion used to insert a table for mounting an object under examination thereon along a horizontal direction;
   a rotary member rotatably supported by said supporting frame, said rotary member being able to rotate around said opening portion;
   a rotation control apparatus for controlling a rotation of said rotary member;
   a first supporting member whose one end is supported at a first position of said rotary member, and which is elongated along a body axial direction of an object under examination;
   an X-ray tube apparatus movably supported on said first supporting member, for irradiating an X-ray to said object under examination;
   a second supporting member whose one end is supported at a second position of said rotary member, and which is elongated along the body axial direction of said object under examination;

a detection apparatus movably supported on said second supporting member, for detecting an X-ray penetrated through said object under examination, which is arranged opposite to said X-ray tube apparatus while sandwiching said object under examination;

an X-ray tube transporting apparatus for transporting said X-ray tube apparatus to an arbitrary position on said first supporting member;

a detection transporting apparatus for transporting said detection apparatus to an arbitrary position on said second supporting member;

an X-ray radiation direction control apparatus for controlling an angle of said X-ray tube apparatus with respect to said body axial direction;

an X-ray image receiving direction apparatus for controlling an angle of said detection apparatus with respect to said body axial direction;

a control apparatus for setting an irradiation angle of an X-ray substantially along said body axial direction of said object under examination to an arbitrary irradiation angle by controlling said X-ray radiation direction control apparatus, and also for arranging said detection apparatus to axially oppose said X-ray tube apparatus in correspondence with said arbitrary irradiation angle set by controlling said X-ray image receiving direction apparatus;

a first image processing apparatus for producing a three-dimensional image from a first output signal from said detection apparatus, said first output signal being obtained by irradiating an X-ray to said object in a first case that said rotary member is rotated under condition that said X-ray tube apparatus and said detection apparatus maintain an axially opposing positional relationship and/or said X-ray tube apparatus and said detection apparatus are respectively slid along said first and second supporting members under condition that said X-ray tube apparatus and said detection apparatus maintain an axially opposing positional relationship or in a second case that said rotary member is rotated under condition that said X-ray tube apparatus and said detection apparatus maintain an axially opposing positional relationship while said table is moved in said body axial direction;

a second image processing apparatus for producing a two-dimensional image from a second output signal from said detection apparatus, said second output signal being obtained by irradiating an X-ray to said object under examination in an X-ray fluoroscopic operation; and a display apparatus for displaying the image produced by said image processing apparatus.

25. A medical X-ray apparatus as claimed in claim 24, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

26. A medical X-ray apparatus comprising:

a supporting frame;

a rotary member rotatably supported by said supporting frame;

a rotation control apparatus for controlling a rotation of said rotary member;

a first arc-shaped supporting member whose one end is supported at a first position of said rotary member, and which is elongated along a body axial direction of an object under examination;

an X-ray tube apparatus movably supported on said first arc-shaped supporting member, for irradiating an X-ray to said object under examination;

a second arc-shaped supporting member whose one end is supported at a second position of said rotary member, and which is elongated along the body axial direction of said object under examination;

a detection apparatus movably supported on said second arc-shaped supporting member, for detecting an X-ray penetrated through said object under examination, which is arranged opposite to said X-ray tube apparatus while sandwiching said object under examination;

an X-ray tube transporting apparatus for transporting said X-ray tube apparatus to an arbitrary position on said first arc-shaped supporting member within a curvature plane where an iso-center is located as a center of said first arc-shaped supporting member;

a detection transporting apparatus for transporting said detection apparatus to an arbitrary position on said second arc-shaped supporting member within a curvature plane where an iso-center is located as a center of said second arc-shaped supporting member;

a control apparatus for setting an irradiation angle of an X-ray substantially body axial direction of said object under examination to an arbitrary irradiation angle, and also for arranging said detection apparatus to axially oppose said X-ray tube apparatus in correspondence with said arbitrary irradiation angle set;

a first image processing apparatus for producing a three-dimensional image from a first output signal from said detection apparatus, said first output signal being obtained by irradiating an X-ray to said object under examination in a case that said rotary member is rotated under condition that said X-ray tube apparatus and said detection apparatus maintain an axially opposing positional relationship and/or said X-ray tube apparatus and said detection apparatus are respectively slid along said first and second supporting members under condition that said X-ray tube apparatus and said detection apparatus maintain an axially opposing positional relationship;

a second image processing apparatus for producing a two-dimensional image from a second output signal from said detection apparatus, said second output signal being obtained by irradiating an X-ray to said object under examination in an X-ray fluoroscopic operation; and a display apparatus for displaying the image produced by said image processing apparatus.

27. A medical X-ray apparatus according to claim 26, wherein each of said first and second arc-shaped supporting members has a length enough to accept an entire portion of said object under examination.

28. A medical X-ray apparatus as claimed in claim 26, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

29. A medical X-ray apparatus comprising:

a supporting frame;

a rotary member rotatably supported by said supporting frame;

a rotation control apparatus for controlling a rotation of said rotary member;

a first supporting member whose one end is supported at a first position of said rotary member, and which is elongated along a body axial direction of an object under examination;

an X-ray tube apparatus movably supported on said first supporting member, for irradiating an X-ray to said object under examination;

a second supporting member whose one end is supported at a second position of said rotary member, and which is elongated along the body axial direction of said object under examination;

a detection apparatus movably supported on said second supporting member, for detecting an X-ray penetrated through said object under examination, which is arranged opposite to said X-ray tube apparatus while sandwiching said object under examination;

an X-ray tube transporting apparatus for transporting said X-ray tube apparatus to an arbitrary position on said first supporting member;

a detection transporting apparatus for transporting said detection apparatus to an arbitrary position on said second supporting member;

an X-ray radiation direction control apparatus for controlling an angle of said X-ray tube apparatus with respect to said body axial direction;

an X-ray image receiving direction apparatus for controlling an angle of said detection apparatus with respect to said body axial direction;

a control apparatus for setting an irradiation angle of an X-ray substantially said body axial direction of said object under examination to an arbitrary irradiation angle by controlling said X-ray radiation direction control apparatus, and also for arranging said detection apparatus to axially oppose said X-ray tube apparatus in correspondence with said arbitrary irradiation angle set by controlling said X-ray image receiving direction apparatus;

a first image processing apparatus for producing a three-dimensional image from a first output signal from said detection apparatus, said first output signal being obtained by irradiating an X-ray to said object under examination in a case that said rotary member is rotated under condition that said X-ray tube apparatus and said detection apparatus maintain an axially opposing positional relationship and/or said X-ray tube apparatus and said detection apparatus are respectively slid along said first and second supporting members under condition that said X-ray tube apparatus and said detection apparatus maintain an axially opposing positional relationship;

a second image processing apparatus for producing a two-dimensional image from a second output signal from said detection apparatus, said second output signal being obtained by irradiating an X-ray to said object under examination in an X-ray fluoroscopic operation; and a display apparatus for displaying the image produced by said image processing apparatus.

30. A medical X-ray apparatus according to claim 29, wherein each of said first and second supporting members has a length enough to accept an entire portion of said object under examination.

31. A medical X-ray apparatus as claimed in claim 29, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

32. A method of obtaining a tomographic image using a medical X-ray apparatus comprising:

a supporting frame;

a rotary member rotatably supported by said supporting frame;

a rotation control apparatus for controlling a rotation of said rotary member;

a first arc-shaped supporting member whose one end is supported at a first position of said rotary member, and which is elongated along a body axial direction of an object under examination;

an X-ray tube apparatus movably supported on said first arc-shaped supporting member, for irradiating an X-ray to said object under examination;

a second arc-shaped supporting member whose one end is supported at a second position of said rotary member, and which is elongated along the body axial direction of said object under examination;

a detection apparatus movably supported on said second arc-shaped supporting member, for detecting an X-ray penetrated through said object under examination, which is arranged opposite to said X-ray tube apparatus while sandwiching said object under examination;

an X-ray tube transporting apparatus for transporting said X-ray tube apparatus to an arbitrary position on said first arc-shaped supporting member within a curvature plane where an iso-center is located as a center of said first arc-shaped supporting member;

a detection transporting apparatus for transporting said detection apparatus to an arbitrary position on said second arc-shaped supporting member within a curvature plane where an iso-center is located as a center of said second arc-shaped supporting member;

a control apparatus for setting an irradiation angle of an X-ray substantially said body axial direction of said object under examination to an arbitrary irradiation angle, and also for arranging said detection apparatus to axially oppose said X-ray tube apparatus in correspondence with said arbitrary irradiation angle set;

an image processing apparatus for processing an output signal from said detection apparatus so as to produce a two-dimensional image and a three-dimensional image; and a display apparatus for displaying the image produced by said image processing apparatus, said method comprising the steps of:

setting a portion to be imaged at said iso-center;

arranging said detection apparatus to axially oppose said X-ray tube apparatus in correspondence with said arbitrary angle set;

irradiating an X-ray to said object under examination while said X-ray tube apparatus and said X-ray image receiving apparatus are mutually slid along reverse directions in an arc manner, wherein the iso-center is employed as a fulcrum; and obtaining a tomographic image of a plane which is located in parallel to a body axis of said object under examination.

33. The method as claimed in claim 32, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

34. A method of obtaining a tomographic image using a medical X-ray apparatus comprising:

a supporting frame;

a rotary member rotatably supported by said supporting frame;

a rotation control apparatus for controlling a rotation of said rotary member;

a first supporting member whose one end is supported at a first position of said rotary member, and which is elongated along a body axial direction of an object under examination;

an X-ray tube apparatus movably supported on said first supporting member, for irradiating an X-ray to said object under examination;

a second supporting member whose one end is supported at a second position of said rotary member, and which is elongated along the body axial direction of said object under examination;

a detection apparatus movably supported on said second supporting member, for detecting an X-ray penetrated through said object under examination, which is arranged opposite to said X-ray tube apparatus while sandwiching said object under examination;

an X-ray tube transporting apparatus for transporting said X-ray tube apparatus to an arbitrary position on said first supporting member;

a detection transporting apparatus for transporting said detection apparatus to an arbitrary position on said second supporting member;

an X-ray radiation direction control apparatus for controlling an angle of said X-ray tube apparatus with respect to said body axial direction;

an X-ray image receiving direction apparatus for controlling an angle of said detection apparatus substantially along said body axial direction;

a control apparatus for setting an irradiation angle of an X-ray with respect to said body axial direction of said object under examination to an arbitrary irradiation angle by controlling said X-ray radiation direction control apparatus, and also for arranging said detection apparatus to axially oppose said X-ray tube apparatus in correspondence with said arbitrary irradiation angle set by controlling said X-ray image receiving direction apparatus;

an image processing apparatus for processing an output signal from said detection apparatus so as to produce a two-dimensional image and a three-dimensional image; and a display apparatus for displaying the image produced by said image processing apparatus, said method comprising the steps of:

setting a portion to be imaged at an iso-center;

arranging said detection apparatus to axially oppose said X-ray tube apparatus in correspondence with said arbitrary angle set;

irradiating an X-ray to said object under examination while said X-ray tube apparatus and said X-ray image receiving apparatus are mutually slid along reverse directions in a linear fashion, wherein the iso-center is employed as a fulcrum; and obtaining a tomographic image of a plane which is located in parallel to a body axis of said object under examination.

35. The method as claimed in claim 34, wherein said X-ray tube apparatus and said detection apparatus are arranged so that perpendicular focal planes extending from said X-ray tube apparatus and said detection apparatus are substantially co-axially aligned with one another substantially along said arbitrary irradiation angle.

* * * * *